(12) United States Patent
Heitsch et al.

(10) Patent No.: US 6,350,778 B1
(45) Date of Patent: Feb. 26, 2002

(54) CINNAMOYLAMINOALKYL-SUBSTITUTED BENZENESULFONAMIDE DERIVATIVES, PROCESSES FOR THEIR PREPARATION, THEIR USE, AND PHARMACEUTICAL PREPARATIONS COMPRISING THEM

(75) Inventors: Holger Heitsch, Mainz-Kastel; Heinrich Christian Englert, Hofheim; Klaus Wirth, Kriftel; Heinz Gögelein, Frankfurt am Main, all of (DE)

(73) Assignee: Aventis Pharma Deutschland GmbH, Frankfurt am Main (DE)

(*) Notice: Subject to any disclaimer, the term of this patent is extended or adjusted under 35 U.S.C. 154(b) by 0 days.

(21) Appl. No.: 09/573,166

(22) Filed: May 19, 2000

(30) Foreign Application Priority Data

May 20, 1999 (DE) .......................... 199 23 086

(51) Int. Cl.⁷ ..................... A61K 31/34; A61K 31/175
(52) U.S. Cl. ..................... 514/471; 514/478; 514/584; 514/593; 514/604; 549/496; 560/13; 564/27; 564/40; 564/86
(58) Field of Search ............... 564/27, 40, 86; 549/496; 514/471, 584, 593, 478, 604; 560/13

(56) References Cited

U.S. PATENT DOCUMENTS

| | | | |
|---|---|---|---|
| 3,454,636 A | 7/1969 | Aumuller et al. | 260/553 |
| 3,507,961 A | 4/1970 | Weber et al. | 424/275 |
| 3,998,968 A | * 12/1976 | Hitzel et al. | 424/321 |
| 4,066,639 A | 1/1978 | Weber et al. | 260/239 BF |
| 5,476,850 A | 12/1995 | Englert et al. | 514/239.5 |
| 5,574,069 A | 11/1996 | Englert et al. | 514/586 |
| 5,652,268 A | 7/1997 | Englert et al. | 514/584 |
| 5,698,596 A | 12/1997 | Englert et al. | 514/586 |

FOREIGN PATENT DOCUMENTS

| | | |
|---|---|---|
| DE | 1 433 878 | 12/1968 |
| DE | 1 518 877 | 1/1969 |
| DE | 1 518 816 | 4/1969 |
| DE | 1 545 810 | 12/1969 |
| EP | 0 612 724 A1 | 8/1994 |
| WO | 00/03978 | 1/2000 |
| WO | 00/15204 | 3/2000 |

OTHER PUBLICATIONS

D. Evans et al., "Synthesis of Diaryl Ethers through the Copper–Promoted Arylation of Phenols with Arylboronic Acids. An Expedient Synthesis of Thyroxine," *Tetrahedron Letters*, 39:2937–2940 (1998).

P. Rocca et al., "A New Convergent Synthesis of alpha–Substituted–beta–Carbolines," *Tetrahedron*, 49(16):3325–3342 (1993).

A. Weichert et al., "Palladium(0) Catalyzed Cross Coupling Reactions of Hindered, Double Activated Aryl Halides with Organozinc Reagents—The Effects of Copper(I) Cocatalysis," *Synlett*, May 1996, pp. 473–474.

P. Schwartz, "The ATRAMI Prospective Study: Implications for Risk Stratification after Myocardial Infarction," *Cardiac Electrophysiology Review*, 2:38–40 (1998).

T. Kinugawa et al., "Altered vagal and sympathetic control of heart rate in left ventricular dysfunction and heart failure," *Am. J. Physiol.*, 37:R310–316 (1995).

E. Vanoli et al., "Vagal Stimulation and Prevention of Sudden Death in Conscious Dogs With a Healed Myocardial Infarction," *Circulation Research*, 68(5):1471–1481 (1991).

A. Burger et al., "Short– and Long–Term Reproducibility of Heart Rate Variability in Patients With Long–Standing Type I Diabetes Mellitus," *Am. J. Cardiol.*, 80:1198–1202 (1997).

W. Linz et al., "Cardiovascular Effects of the Novel Potassium Channel Opener (3S,4R)–3–Hydroxy . . . ," *Arzneim.-Forsch./Drug Res.*, 42 (II):1180–1185 (1992).

J. Lawson, "Antiarrhythmic Activity of Some Isoquinoline Derivatives Determined By a Rapid Screening Procedure in the Mouse," *J. Pharmacol. Exp. Ther.*, 160(5):22–31 (1968).

* cited by examiner

Primary Examiner—Peter O'Sullivan
(74) Attorney, Agent, or Firm—Finnegan, Henderson, Farabow, Garrett & Dunner, L.L.P.

(57) ABSTRACT

The present invention relates to cinnamoylaminoalkyl-substituted benzenesulfonamide derivatives of formula I

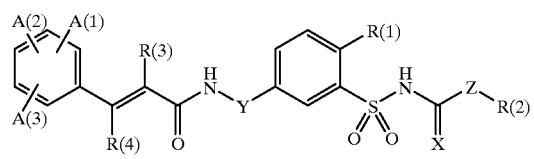

in which A(1), A(2), A(3), R(1), R(2), R(3), R(4), X, Y, and Z have the meanings indicated in the claims. Compounds of formula I are valuable pharmaceutical active compounds which exhibit, for example, an inhibitory action on ATP-sensitive potassium channels in the cardiac muscle and/or in the cardiac nerve and are suitable, for example, for the treatment of disorders of the cardiovascular system such as coronary heart disease, arrhythmias, cardiac insufficiency or cardiomyopathies, or for the prevention of sudden cardiac death, or for improving decreased contractility of the heart. The invention furthermore relates to processes for the preparation of compounds of formula I, their use, and pharmaceutical preparations comprising them.

20 Claims, No Drawings

CINNAMOYLAMINOALKYL-SUBSTITUTED BENZENESULFONAMIDE DERIVATIVES, PROCESSES FOR THEIR PREPARATION, THEIR USE, AND PHARMACEUTICAL PREPARATIONS COMPRISING THEM

The present invention relates to cinnamoylaminoalkyl-substituted benzenesulfonamide derivatives of formula I

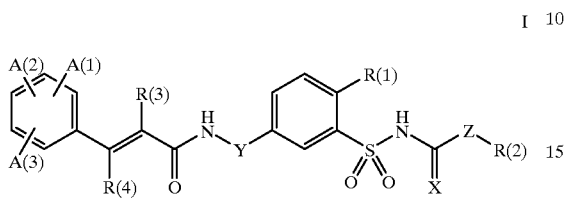

in which A(1), A(2), A(3), R(1), R(2), R(3), R(4), X, Y, and Z have the meanings indicated below. Compounds of formula I are valuable pharmaceutical active compounds which exhibit, for example, an inhibitory action on ATP-sensitive potassium channels in the cardiac muscle and/or in the cardiac nerve and are suitable, for example, for the treatment of disorders of the cardiovascular system such as coronary heart disease, arrhythmias, cardiac insufficiency, or cardiomyopathies, or for the prevention of sudden cardiac death or for improving decreased contractility of the heart. The invention furthermore relates to processes for the preparation of compounds of formula I, their use, and pharmaceutical preparations comprising them.

A hypoglycemic action is described for certain benzenesulfonylureas. Glibenclamide, which is used therapeutically as an agent for the treatment of diabetes mellitus, counts as a prototype of hypoglycemic sulfonylureas of this type. Glibenclamide blocks ATP-sensitive potassium channels and is used in research as a tool for the exploration of potassium channels of this type. In addition to its hypoglycemic action, glibenclamide additionally possesses other actions that are attributed to the blockade of precisely these ATP-sensitive potassium channels, which as yet, however, still cannot be utilized therapeutically. These include, in particular, an antifibrillatory action on the heart. In the treatment of ventricular fibrillation or its early stages with glibenclamide, however, the marked hypoglycemia simultaneously produced by this substance would be undesirable or even dangerous, as it can further worsen the condition of the patient.

Various patent applications, for example U.S. Pat. No. 5,698,596, U.S. Pat. No. 5,476,850, or U.S. Pat. No. 5,652,268 and WO-A-00/03978 (German Patent Application 19832009.4), disclose antifibrillatory benzenesulfonylureas and -thioureas having decreased hypoglycemic action. WO-A-00/15204 (German Patent Application 19841534.6) describes the action of some of these compounds on the autonomic nervous system. The properties of these compounds, however, are not satisfactory in various respects, and there furthermore exists a need for compounds having a more favorable pharmacodynamic and pharmacokinetic property profile, which are better suited, in particular, to the treatment of a disturbed heart rhythm and its consequences. Various benzenesulfonylureas having an acylaminoalkyl substituent in which the acyl group can also be derived, inter alia, from cinnamic acids, are disclosed in German Laid-Open Specifications DE-A-1443878, DE-A-1518816, DE-A-1518877, and DE-A-1545810. These compounds have a hypoglycemic action, but an action on the heart is not known as yet. Surprisingly, it has now been found that certain cinnamoylaminoalkyl-substituted benzenesulfonamide derivatives are distinguished by a marked action on ATP-sensitive potassium channels in the heart and further advantageous pharmacological actions.

One subject of the present invention are compounds of formula I

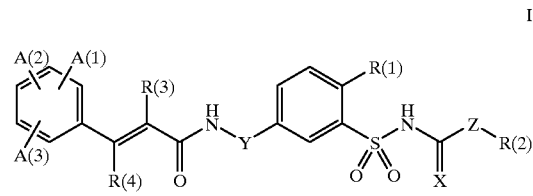

in which:

X is oxygen, sulfur, or cyanoimino;

Y is —(CR(5)$_2$)$_n$—;

Z is NH or oxygen;

the residues A(1), A(2), and A(3), which are independent of one another and can be identical or different, are hydrogen, halogen, ($C_1$–$C_4$)-alkyl, ($C_1$–$C_4$)-alkoxy, methylenedioxy, formyl, or trifluoromethyl;

R(1) is a) ($C_1$–$C_4$)-alkyl;

b) —O—($C_1$–$C_4$)-alkyl;

c) —O—($C_1$–$C_4$)-alkyl—E(1)—($C_1$–$C_4$)-alkyl-D(1), in which D(1) is hydrogen or —E(2)—($C_1$–$C_4$)-alkyl-D(2), in which D(2) is hydrogen or —E(3)—($C_1$–$C_4$)-alkyl, where E(1), E(2), and E(3), which are independent of one another and can be identical or different, are O, S, or NH;

d) —O—($C_1$–$C_4$)-alkyl which is substituted by a residue of a saturated 4-membered to 7-membered heterocycle which contains one or two oxygens as ring heteroatoms;

e) —O—($C_2$–$C_4$)-alkenyl;

f) —O—($C_1$–$C_4$)-alkyl-phenyl in which the phenyl group is unsubstituted or substituted by one or two identical or different substituents selected from halogen, ($C_1$–$C_4$)-alkyl, ($C_1$–$C_4$)-alkoxy, and trifluoromethyl;

g) —O-phenyl which is unsubstituted or substituted by one or two identical or different substituents selected from halogen, ($C_1$–$C_4$)-alkyl, ($C_1$–$C_4$)-alkoxy, and trifluoromethyl;

h) halogen;

i) phenyl which is unsubstituted or substituted by one or two identical or different substituents selected from halogen, ($C_1$–$C_4$)-alkyl, ($C_1$–$C_4$)-alkoxy, —S(O)$_m$—($C_1$–$C_4$)-alkyl, phenyl, amino, hydroxy, nitro, trifluoromethyl, cyano, hydroxycarbonyl, carbamoyl, ($C_1$–$C_4$)-alkoxycarbonyl, and formyl;

j) ($C_2$–$C_5$)-alkenyl which is unsubstituted or substituted by a substituent selected from phenyl, cyano, hydroxycarbonyl, and ($C_1$–$C_4$)-alkoxycarbonyl;

k) ($C_2$–$C_5$)-alkynyl which is unsubstituted or substituted by a substituent selected from phenyl and ($C_1$–$C_4$)-alkoxy;

l) monocyclic or bicyclic heteroaryl having one or two identical or different ring heteroatoms selected from oxygen, sulfur, and nitrogen;

m) —S(O)$_m$-phenyl which is unsubstituted or substituted by one or two identical or different substituents selected from halogen, $(C_1-C_4)$-alkyl, $(C_1-C_4)$-alkoxy, and trifluoromethyl; or n) —S(O)$_m$—$(C_1-C_4)$-alkyl;

R(2) is hydrogen, $(C_1-C_6)$-alkyl, or $(C_3-C_7)$-cycloalkyl, but is not hydrogen if Z is oxygen;

the residues R(3) and R(4), which are independent of one another and can be identical or different, are phenyl which is unsubstituted or substituted by one or two identical or different substituents selected from halogen, $(C_1-C_4)$-alkyl, $(C_1-C_4)$-alkoxy, and trifluoromethyl, hydrogen, or $(C_1-C_4)$-alkyl;

the residues R(5), which are independent of one another and can be identical or different, are hydrogen or $(C_1-C_3)$-alkyl;

m is 0, 1, or 2;

n is 1, 2, 3, or 4;

in any stereoisomeric form or mixture thereof in any ratio, or a physiologically tolerable salt thereof, where compounds of formula I are excluded in which, simultaneously, X is oxygen, Z is NH, R(1) is halogen, $(C_1-C_4)$-alkyl, or —O—$(C_1-C_4)$-alkyl, and R(2) is $(C_2-C_6)$-alkyl or $(C_5-C_7)$-cycloalkyl.

If groups, residues, substituents, or variables can occur several times in compounds of formula I, they can all independently of one another have the meanings indicated and can in each case be identical or different.

The term alkyl denotes straight-chain or branched saturated hydrocarbon residues. This also applies to residues derived therefrom such as, for example, alkoxy, alkoxycarbonyl, or the residue —S(O)$_m$-alkyl. Examples of alkyl residues are methyl, ethyl, n-propyl, isopropyl, n-butyl, sec-butyl, isobutyl, tert-butyl, n-pentyl, 1-methylbutyl, isopentyl, neopentyl, tert-pentyl, n-hexyl, or isohexyl. Examples of alkoxy are methoxy, ethoxy, n-propoxy, isopropoxy, or tert-butoxy. The same applies to substituted alkyl residues, for example phenyl-alkyl-residues, or to divalent alkyl residues (alkanediyl residues), in which the substituents or the bonds via which the residues are bonded to the neighboring groups can be situated in any desired positions. Examples of alkyl residues of this type, which are bonded to two neighboring groups and which, inter alia, can represent the group Y, are —CH$_2$—, —CH(CH$_3$)—, —C(CH$_3$)$_2$—, —CH$_2$—CH$_2$—, —CH(CH$_3$)—CH$_2$—, —CH$_2$—CH(CH$_3$)—, —CH$_2$—CH$_2$—CH$_2$—, or —CH$_2$—CH$_2$—CH$_2$—CH$_2$—.

Alkenyl and alkynyl denote straight-chain or branched, mono- or polyunsaturated hydrocarbon residues, in which the double bonds and/or triple bonds can be situated in any desired positions. Preferably, the residues alkenyl and alkynyl contain one double bond or one triple bond. Examples of alkenyl and alkynyl are vinyl, prop-2-enyl (allyl), prop-1-enyl, but-2-enyl, but-3-enyl, 3-methylbut-2-enyl, pent-2,4-dienyl, ethynyl, prop-2-ynyl (propargyl), prop-1-ynyl, but-2-ynyl, and but-3-ynyl. In substituted alkenyl residues and alkynyl residues, the substituents can be situated in any desired positions.

Examples of cycloalkyl residues are cyclopropyl, cyclobutyl, cyclopentyl, cyclohexyl, or cycloheptyl.

Halogen is fluorine, chlorine, bromine, or iodine, preferably chlorine or fluorine.

In substituted phenyl residues, the substituents can be situated in any desired positions. In monosubstituted phenyl residues, the substituent can be situated in the 2-position, the 3-position, or the 4-position. In disubstituted phenyl residues, the substituents can be situated in the 2,3-position, 2,4-position, 2,5-position, 2,6-position, 3,4-position, or 3,5-position. If a phenyl residue carries three substituents, these can be situated in the 2,3,4-position, 2,3,5-position, 2,3,6-position, 2,4,5-position, 2,4,6-position, or 3,4,5-position. If a phenyl residue carries a further phenyl residue as a substituent, this second phenyl residue can also be unsubstituted or substituted by the substituents which are given for the first phenyl residue (apart from by a phenyl residue).

Heteroaryl is understood as meaning residues of monocyclic or bicyclic aromatic ring systems, which in the case of the monocyclic systems have a 5-membered ring or a 6-membered ring, and in the case of the bicyclic systems have two fused 5-membered rings, a 6-membered ring fused to a 5-membered ring, or two fused 6-membered rings. The heteroaryl residues can be conceived as being residues derived from cyclopentadienyl, phenyl, pentalenyl, indenyl, or naphthyl by replacement of one or two CH groups and/or CH$_2$ groups by S, O, N, NH (or N carrying a substituent such as, for example, N—CH$_3$), where the aromatic ring system is retained or an aromatic ring system is formed. In addition to the one or two ring heteroatoms, they contain three to nine ring carbons. Examples of heteroaryl are, in particular, furyl, thienyl, pyrrolyl, imidazolyl, pyrazolyl, 1,3-oxazolyl, 1,2-oxazolyl, 1,3-thiazolyl, 1,2-thiazolyl, pyridyl, pyrazinyl, pyrimidyl, pyridazinyl, indolyl, benzofuranyl, quinolyl, isoquinolyl, or benzopyranyl. A heteroaryl residue can be bonded via any suitable carbon. For example, a thienyl residue can be present as a 2-thienyl residue or 3-thienyl residue, a furyl residue as a 2-furyl residue or 3-furyl residue, and a pyridyl residue as a 2-pyridyl residue, 3-pyridyl residue, or 4-pyridyl residue. A residue which is derived from 1,3-thiazole or from imidazole can be bonded via the 2-position, the 4-position, or the 5-position. Suitable nitrogen heterocycles can also be present as N-oxides or as quaternary salts having an anion derived from a physiologically tolerable acid as a counterion. Pyridyl residues can be present, for example, as pyridine N-oxides.

If two ring oxygens are present in a saturated 4-membered to 7-membered heterocycle containing one or two oxygens as ring heteroatoms, these are not bonded directly to one another, but at least one ring carbon is situated between them. Examples of saturated 4-membered to 7-membered heterocycles which contain one or two oxygens as ring heteroatoms are oxetane, tetrahydrofuran, tetrahydropyran, oxepane, 1,3-dioxolane, or 1,4-dioxane. Preferred heterocycles are those which contain one ring oxygen. Particularly preferred heterocycles are tetrahydrofuran and tetrahydropyran. The saturated oxygen heterocycles can be bonded via any ring carbon, oxetane, for example, via the 2-position or the 3-position, tetrahydrofuran via the 2-position or the 3-position, tetrahydropyran via the 2-position, the 3-position, or the 4-position, 1,3-dioxolane via the 2-position or the 4-position. Tetrahydrofuran and tetrahydropyran are preferably bonded via the 2-position.

The present invention includes any stereoisomeric form of compounds of formula I. Asymmetric centers present in compounds of formula I can all independently of one another have the S configuration or the R configuration or the compounds can be present as an R/S mixture with respect to any of the asymmetric centers. The invention includes all possible enantiomers and diastereomers, as well as mixtures of at least two stereoisomeric forms, for example mixtures of enantiomers and/or diastereomers, in any ratio. Enantiomers, for example, are thus a subject of the invention in enantiomerically pure form, both as levorotatory and as dextrorotatory antipodes, in the form of racemates, and in the form of mixtures of the two enantiomers in any ratio. In the presence of cis/trans isomerism (or E/Z isomerism), both the cis form and the trans form and mixtures of these forms in any ratio are a subject of the invention. The preparation of individual stereoisomers can be carried out, if desired, by separation of a mixture according to customary methods, for example by chromatography or crystallization, or by use of stereochemically uniform starting substances in the synthesis or by stereoselective reactions. If appropriate, a derivatization or salt formation can be carried out before separation of stereoisomers. The separation of a stereoisomer mixture can be carried out at the stage of compounds of formula I or at the stage of an intermediate in the course of the synthesis. The invention also includes all tautomeric forms of compounds of formula I.

Physiologically tolerable salts of compounds of formula I are, in particular, nontoxic salts or pharmaceutically utilizable salts. They can contain inorganic or organic salt components. Such salts can be prepared, for example, from compounds of formula I which contain at least one acidic group, and nontoxic inorganic or organic bases. Possible bases are, for example, suitable alkali metal compounds or alkaline earth metal compounds, such as sodium hydroxide or potassium hydroxide, or ammonia or organic amino compounds or quaternary ammonium hydroxides. Reactions of compounds of formula I with bases for the preparation of the salts are in general carried out in a solvent or diluent according to customary procedures. On account of the physiological and chemical stability, advantageous salts are, in the presence of acidic groups, in many cases sodium, potassium, magnesium, or calcium salts or ammonium salts which can carry at least one organic residue on the nitrogen. Salt formation on the nitrogen of the benzenesulfonamide group leads to compounds of formula II

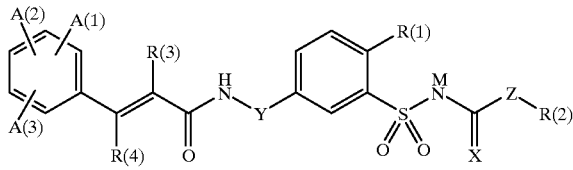

II in which A(1), A(2), A(3), R(1), R(2), R(3), R(4), X, Y, and Z have the meanings indicated above, and the cation M, for example, is an alkali metal ion or an equivalent of an alkaline earth metal ion, for example the sodium, potassium, magnesium, or calcium ion, or the unsubstituted ammonium ion or an ammonium ion having at least one organic residue. An ammonium ion which is M can also be, for example, the cation which is obtained from an amino acid by protonation, in particular a basic amino acid such as, for example, lysine or arginine.

Compounds of formula I which contain at least one basic, that is protonatable, group can be present in the form of their acid addition salts with physiologically tolerable inorganic or organic acids and are used according to the invention, for example, as salts with hydrogen chloride, phosphoric acid, sulfuric acid, or organic carboxylic acids or sulfonic acids such as, for example, p-toluenesulfonic acid, acetic acid, tartaric acid, benzoic acid, fumaric acid, maleic acid, or citric acid. Acid addition salts can also be obtained from compounds of formula I by customary processes known to the person skilled in the art, for example by combination with an organic or inorganic acid in a solvent or diluent. If compounds of formula I simultaneously contain acidic and basic groups in the molecule, the present invention also includes, in addition to the salt forms described, inner salts or betaines (zwitterions). The present invention also includes all salts of compounds of formula I which, because of low physiological tolerability, are not directly suitable for use in pharmaceuticals, but are suitable, for example, as intermediates for chemical reactions or for the preparation of physiologically tolerable salts, for example by anion exchange or cation exchange.

The present invention furthermore includes all solvates of compounds of formula I, for example hydrates or adducts with alcohols, and also derivatives of compounds of formula I such as, for example, esters and amides of acid groups, and prodrugs and active metabolites of compounds of formula I.

In compounds of formula I, X is preferably oxygen or sulfur. A particularly preferred group of compounds is formed by those compounds in which X is sulfur and Z is NH. In compounds of formula I in which Z is oxygen, X is particularly preferably oxygen. A particularly preferred group of compounds of formula I is also formed by those compounds in which X is oxygen and, simultaneously, R(4) is hydrogen or ($C_1$–$C_4$)-alkyl, where in a very particularly preferred subgroup of these compounds R(2) is methyl.

Y is preferably the residue —$(CR(5)_2)_n$— in which the residues R(5) are hydrogen or methyl, particularly preferably hydrogen. n is preferably 2 or 3, particularly preferably 2. An especially preferred group Y is the group —$CH_2$—$CH_2$—.

Z is preferably NH, that is preferred compounds of formula I are benzenesulfonamide derivatives of formula Ia

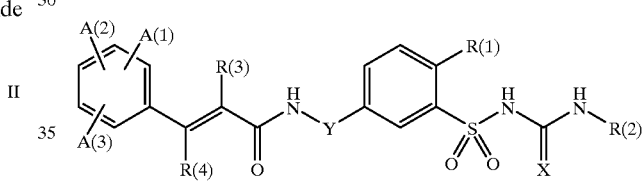

Ia in which A(1), A(2), A(3), R(1), R(2), R(3), R(4), X, and Y have the meanings indicated above, in any stereoisomeric form or mixture thereof in any ratio, or a physiologically tolerable salt thereof. Particularly preferred compounds of formula Ia are those compounds in which X is oxygen or sulfur, that is compounds that are benzenesulfonylurea derivatives or benzenesulfonylthiourea derivatives.

The residues A(1), A(2), and A(3) can be situated in any desired positions in the phenyl ring to which they are bonded, as was generally explained above with respect to substituents in phenyl residues. If one of the residues A(1), A(2), or A(3) is hydrogen and the two others have a meaning other than hydrogen, the two residues different from hydrogen are preferably in the 2,4-position. The positions in the phenyl residue to which none of the residues A(1), A(2), and A(3) are bonded carry hydrogens. Preferably, one of the residues A(1), A(2), or A(3) is hydrogen and the two others are identical or different residues selected from hydrogen, halogen, ($C_1$–$C_4$)-alkyl, ($C_1$–$C_4$)-alkoxy, methylenedioxy, formyl, and trifluoromethyl, that is the phenyl residue carrying the residues A(1), A(2), and A(3) is preferably unsubstituted or substituted by one or two identical or different substituents. Particularly preferably, one of the residues A(1), A(2), or A(3) is hydrogen, one of the residues A(1), A(2), or A(3) is hydrogen, halogen, ($C_1$–$C_4$)-alkyl, ($C_1$–$C_4$)-alkoxy, methylenedioxy, formyl, or trifluoromethyl, and one of the residues A(1), A(2), or A(3) is halogen, ($C_1$–$C_4$)-alkyl, ($C_1$–$C_4$)-alkoxy, methylenedioxy, formyl, or trifluoromethyl, that is the phenyl residue carrying the residues A(1), A(2), and A(3) is particularly preferably a substituted phenyl residue which carries one or two identical or different substituents. If the residues A(1), A(2), and A(3) have a meaning other than hydrogen, they are preferably identical or different residues selected from halogen, $(C_1-C_4)$-alkyl, $(C_1-C_4)$-alkoxy, methylenedioxy, and trifluoromethyl, in particular identical or different residues selected from halogen, $(C_1-C_4)$-alkyl, $(C_1-C_4)$-alkoxy, and trifluoromethyl. Especially preferably, the residues A(1), A(2), and A(3) are identical or different residues selected from hydrogen, methyl, methoxy, ethoxy, fluorine, chlorine, and trifluoromethyl. In an especially preferred embodiment, the phenyl residue carrying the residues A(1), A(2), and A(3) is a substituted phenyl residue which carries one or two identical or different substituents selected from methyl, methoxy, ethoxy, fluorine, chlorine, and trifluoromethyl. It is moreover preferred if the phenyl residue carrying the residues A(1), A(2), and A(3) is a 2,4-dimethoxyphenyl residue.

A residue $(C_1-C_4)$-alkyl representing R(1) is preferably one of the residues methyl, ethyl, or isopropyl. A residue —O—$(C_1-C_4)$-alkyl representing R(1) is preferably one of the residues methoxy or ethoxy, in particular methoxy.

In the residue —O—$(C_1-C_4)$-alkyl-E(1)—$(C_1-C_4)$-alkyl-D(1) representing R(1), the groups E(1), E(2), and E(3), which can be present therein, are preferably oxygen. D(1) is preferably hydrogen. If D(1) has a meaning other than hydrogen, D(2) is preferably hydrogen. Preferred meanings of the residue —O—$(C_1-C_4)$-alkyl-E(1)—$(C_1-C_4)$-alkyl-D(1) are —O—$(C_1-C_4)$-alkyl-O—$(C_1-C_4)$-alkyl and —O—$(C_1-C_4)$-alkyl-O—$(C_1-C_4)$-alkyl-O—$(C_1-C_4)$-alkyl, a particularly preferred meaning is —O—$(C_1-C_4)$-alkyl-O—$(C_1-C_4)$-alkyl. Especially preferred meanings of the residue —O—$(C_1-C_4)$-alkyl-E(1)—$(C_1-C_4)$-alkyl-D(1) are 2-methoxyethoxy- and 2-(2-methoxyethoxy)ethoxy-, in particular 2-methoxyethoxy-.

A residue —O—$(C_1-C_4)$-alkyl representing R(1) which is substituted by a residue of an oxygen heterocycle, is preferably one of the residues tetrahydrofuran-2-ylmethoxy or tetrahydropyran-2-ylmethoxy. A residue —O—$(C_2-C_4)$-alkenyl representing R(1) is preferably allyloxy. A residue —O—$(C_1-C_4)$-alkyl-phenyl representing R(1) is preferably benzyloxy. A residue —O-phenyl representing R(1) is preferably unsubstituted or monosubstituted phenoxy, particularly preferably unsubstituted phenoxy or phenoxy substituted in the 4-position, in particular unsubstituted phenoxy, 4-methylphenoxy, 4-methoxyphenoxy, 4-fluorophenoxy, or 4-trifluoromethylphenoxy. Halogen representing R(1) is preferably bromine or iodine.

A phenyl residue representing R(1) is preferably unsubstituted or monosubstituted phenyl, particularly preferably unsubstituted phenyl or phenyl substituted in the 4-position, in particular unsubstituted phenyl, 4-methylphenyl, 4-methoxyphenyl, 4-fluorophenyl, or 4-trifluoromethylphenyl, especially unsubstituted phenyl. A residue $(C_2-C_5)$-alkenyl representing R(1) is preferably allyl. A residue $(C_2-C_5)$-alkynyl representing R(1) is preferably ethynyl. A heteroaryl residue representing R(1) preferably contains one heteroatom and is preferably a monocyclic residue, particularly preferably a pyridyl residue, thienyl residue, or furyl residue, in particular one of the residues 2-pyridyl, 3-pyridyl, 2-thienyl, and 2-furyl, especially 2-furyl.

A residue —S(O)$_m$-phenyl representing R(1) is preferably unsubstituted or monosubstituted —S(O)$_m$-phenyl, particularly preferably unsubstituted —S(O)$_m$-phenyl, especially the unsubstituted residue —S-phenyl. A residue —S(O)$_m$-$(C_1-C_4)$-alkyl which is R(1) is preferably —S(O)$_m$-methyl, in particular —S-methyl.

m is preferably 0 or 2, particularly preferably 0.

R(1) is preferably
a) methyl, ethyl, or isopropyl;
b) methoxy or ethoxy;
c) 2-methoxyethoxy;
d) tetrahydrofuran-2-ylmethoxy or tetrahydropyran-2-ylmethoxy;
e) allyloxy;
f) benzyloxy;
g) phenoxy, 4-methylphenoxy, 4-methoxyphenoxy, 4-fluorophenoxy, or 4-trifluoromethylphenoxy;
h) bromine or iodine;
i) phenyl, 4-methylphenyl, 4-methoxyphenyl, 4-fluorophenyl, or 4-trifluoromethylphenyl;
j) allyl;
k) ethynyl;
l) pyridyl, furyl, or thienyl;
m) —S-phenyl; or
n) —S-methyl.

Particularly preferably, R(1) is one of the residues mentioned in the general or in a preferred definition of R(1) which are bonded to the benzene ring carrying the group R(1) via an oxygen, or an optionally substituted phenyl residue or heteroaryl residue. Very particularly preferably, R(1) is one of the residues methoxy, 2-methoxyethoxy-, tetrahydrofuran-2-ylmethoxy-, tetrahydropyran-2-ylmethoxy-, allyloxy, benzyloxy, and phenoxy, especially preferably one of the residues methoxy and 2-methoxyethoxy.

If Z is NH, R(2) is preferably hydrogen, $(C_1-C_4)$-alkyl, or $(C_3-C_6)$-cycloalkyl, particularly preferably hydrogen, methyl, ethyl, isopropyl, or cyclohexyl. A group of very particularly preferred compounds of formula I in which Z is NH, is formed by compounds in which R(2) is hydrogen or methyl, another group is formed by compounds in which R(2) is methyl, ethyl, isopropyl, or cyclohexyl. If Z is oxygen, R(2) is preferably $(C_1-C_4)$-alkyl. An especially preferred meaning of R(2) is methyl.

R(3) is preferably hydrogen, methyl, or unsubstituted phenyl, particularly preferably hydrogen. R(4) is preferably hydrogen.

Preferred compounds of formula I are those in which at least one of the residues contained therein have preferred meanings, where all combinations of preferred substituent definitions are a subject of the present invention. Also with respect to all preferred compounds of formula I, the present invention includes any stereoisomeric form or mixture thereof in any ratio, or a physiologically tolerable salt thereof. Also from the preferred compounds which are a subject of the present invention per se, those compounds are excluded which are excluded above from the general definition of compounds of formula I by the disclaimer.

Thus, for example, a group of preferred compounds is formed by those compounds of formula I in which Z is NH, X is sulfur, and R(2) is methyl, and the other residues have the general or preferred meanings indicated above, in any stereoisomeric form or mixture thereof in any ratio, or a physiologically tolerable salt thereof.

A group of preferred compounds is also formed by those compounds of formula I, in which:

Y is —CH$_2$—CH$_2$—;

one of the residues A(1), A(2), and A(3) is hydrogen and the other two are identical or different residues selected from hydrogen, methyl, methoxy, ethoxy, fluorine, chlorine, and trifluoromethyl;

R(2) is methyl, ethyl, isopropyl, or cyclohexyl;

R(3) and R(4) are hydrogen; and

R(1), X, and Z have the general or preferred meanings indicated above, in any stereoisomeric form or mixture thereof in any ratio, or a physiologically tolerable salt thereof. Particularly preferred subgroups of these compounds are formed by compounds of formula I in which Z is NH and/or X is sulfur. A very particularly preferred subgroup is formed by compounds of formula I in which R(2) is methyl.

A group of particularly preferred compounds is formed, for example, by compounds of formula Ib Ib

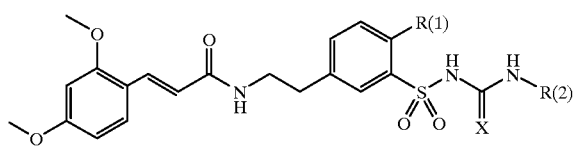

in which:

X is oxygen or sulfur;

R(1) is methoxy, 2-methoxyethoxy-, tetrahydrofuran-2-ylmethoxy-, tetrahydropyran-2-ylmethoxy-, allyloxy, benzyloxy, or phenoxy;

R(2) is methyl, ethyl, isopropyl, or cyclohexyl; in any stereoisomeric form or mixture thereof in any ratio, or a physiologically tolerable salt thereof.

A preferred meaning of R(2) in compounds of formula Ib is methyl. Preferably, the residue X in compounds of formula Ib is sulfur. A group of very particularly preferred compounds is thus formed by compounds of formula Ib in which:

X is sulfur;

R(1) is methoxy, 2-methoxyethoxy-, tetrahydrofuran-2-ylmethoxy-, tetrahydropyran-2-ylmethoxy-, allyloxy, benzyloxy, or phenoxy;

R(2) is methyl, ethyl, isopropyl, or cyclohexyl;

in any stereoisomeric form or mixture thereof in any ratio, or a physiologically tolerable salt thereof, where also in these compounds, R(2) is preferably methyl.

The present invention also relates to processes for the preparation of compounds of formula I which are explained below and by which compounds according to the invention are obtainable.

Compounds of formula I in which X is sulfur and Z is NH, that is benzenesulfonylthioureas of formula Ic Ic

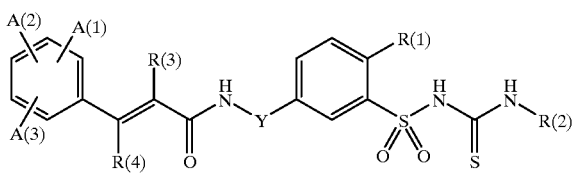

in which A(1), A(2), A(3), R(1), R(2), R(3), R(4), and Y have the abovementioned meanings, can be prepared, for example, by reacting benzenesulfonamides of formula III

III

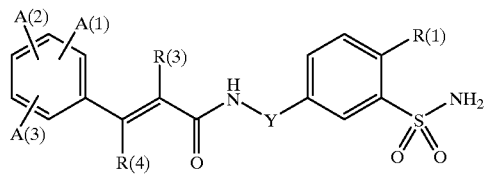

in which A(1), A(2), A(3), R(1), R(3), R(4), and Y have the abovementioned meanings, in an inert solvent or diluent with a base and with an R(2)-substituted isothiocyanate of formula IV

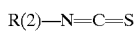   IV in which R(2) has the meanings indicated above. Suitable bases are, for example, alkali metal or alkaline earth metal hydroxides, hydrides, amides, or alkoxides, such as sodium hydroxide, potassium hydroxide, calcium hydroxide, sodium hydride, potassium hydride, calcium hydride, sodium amide, potassium amide, sodium methoxide, sodium ethoxide, potassium tert-butoxide, or quaternary ammonium hydroxides. The reaction of the compound of formula III with the base can first be carried out in a separate step and the initially resulting salt of formula V

V

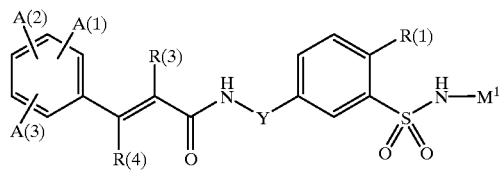

in which A(1), A(2), A(3), R(1), R(3), R(4), and Y have the abovementioned meanings, and $M^1$ is an alkali metal ion, for example sodium or potassium, or an equivalent of an alkaline earth metal ion, for example magnesium or calcium, or an ammonium ion which is inert under the reaction conditions, for example a quaternary ammonium ion, can, if desired, also be intermediately isolated. The salt of formula V, however, can particularly advantageously also be produced in situ from the compound of formula III and reacted directly with the isothiocyanate of formula IV. Suitable inert solvents for the reaction are, for example, ethers such as tetrahydrofuran (THF), dioxane, ethylene glycol dimethyl ether (DME), or diglyme, ketones such as acetone or butanone, nitriles such as acetonitrile, nitro compounds such as nitromethane, esters such as ethyl acetate, amides such as dimethylformamide (DMF) or N-methylpyrrolidone (NMP), hexamethylphosphortriamide (HMPT), sulfoxides such as dimethyl sulfoxide (DMSO), or hydrocarbons such as benzene, toluene, or xylenes. Mixtures of these solvents with one another are furthermore suitable. The reaction of compounds of formula III and/or V with the compound of formula IV is usually carried out at temperatures from room temperature to 150° C.

Compounds of formula I in which X is oxygen and Z is NH, that is benzenesulfonylureas of formula Id

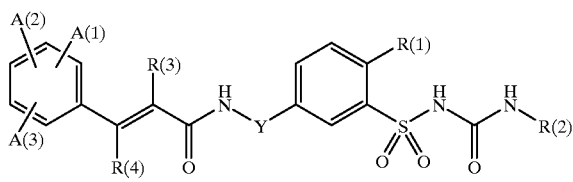

in which A(1), A(2), A(3), R(1), R(2), R(3), R(4), and Y have the abovementioned meanings, can be prepared, for example, by reacting, analogously to the synthesis of thiourea derivatives of formula Ic described above, benzenesulfonamides of formula III and/or their salts of formula V in an inert solvent or diluent with a base and with an R(2)-substituted isocyanate of formula VI

in which R(2) has the meanings indicated above. The above explanations for the reaction with isothiocyanates correspondingly apply to the reaction with isocyanates.

Benzenesulfonylureas of formula Id can also be prepared from benzenesulfonamides of formula IIII and/or their salts of formula V by reaction with R(2)-substituted 2,2,2-trichloroacetamides of formula VII

in which R(2) has the meanings indicated above, in the presence of a base in an inert high-boiling solvent such as, for example, DMSO.

Benzenesulfonylureas of formula Id can also be prepared from the corresponding benzenesulfonylthioureas of formula Ic by a conversion reaction (desulfurization). The replacement of sulfur in the thiourea group of compounds of formula Ic by an oxygen can be carried out, for example, with the aid of oxides or salts of heavy metals or by use of oxidants such as hydrogen peroxide, sodium peroxide, or nitrous acid.

Benzenesulfonylureas and -thioureas of formulae Id and Ic can also be prepared by reaction of amines of formula R(2)—NH$_2$ with benzenesulfonyl isocyanates and isothiocyanates of formula VIII

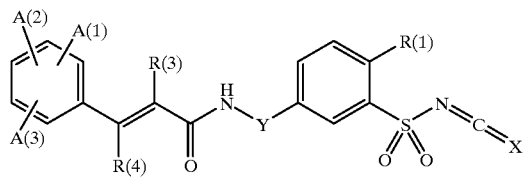

in which A(1), A(2), A(3), R(1), R(3), R(4), and Y have the abovementioned meanings, and X is oxygen or sulfur. Sulfonyl isocyanates of formula VIII (X=oxygen) can be obtained from benzenesulfonamides of formula III according to customary methods, for example using phosgene. Sulfonyl isothiocyanates of formula VIII (X=sulfur) can be prepared by reaction of the sulfonamide of formula III with alkali metal hydroxides and carbon disulfide in an organic solvent such as DMF, DMSO, or NMP. The di-alkali metal salt of the sulfonyidithiocarbamic acid obtained in this case can be reacted in an inert solvent with a slight excess of phosgene or of a phosgene substitute such as triphosgene or with a chloroformic acid ester (2 equivalents) or with thionyl chloride. The solution of the sulfonyl iso(thio)cyanate of formula VIII obtained can be reacted directly with the appropriate substituted amine of formula R(2)—NH$_2$ or, if compounds of formula I are to be prepared in which R(2) is hydrogen, with ammonia.

Correspondingly, starting from benzenesulfonyl iso(thio)cyanates of formula VIII, by means of addition of alcohols of formula R(2)—OH compounds of formula I can be prepared in which Z is oxygen, that is benzenesulfonylurethane derivatives of formula Ie

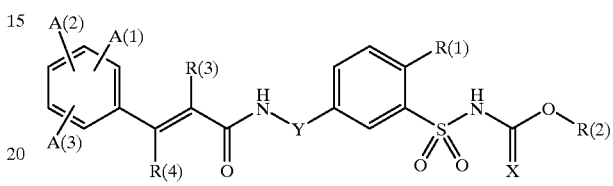

in which A(1), A(2), A(3), R(1), R(2), R(3), R(4), and Y have the abovementioned meanings, but as mentioned R(2) is not hydrogen, and X is oxygen or sulfur. Compounds of formula Ie can also be prepared, for example by reacting, analogously to the syntheses described above, benzenesulfonamides of formula III and/or their salts of formula V in an inert solvent, for example a high-boiling ether, with reactive carbonic acid derivatives, for example with chloroformic acid esters of formula Cl—CO—OR(2) or pyrocarbonic acid diesters of formula (R(2)O—C(=O))$_2$O. Starting from compounds of formula Ie in which X is oxygen, compounds of formula Id are obtainable by action of the appropriate amine of formula R(2)—NH$_2$ in an inert high-boiling solvent, for example toluene, at temperatures up to the boiling point of the respective solvent.

Compounds of formula I in which X is the cyanoimino group =N—CN are obtainable, for example, by reacting diphenyl N-cyanoiminocarbonates of formula NC—N=C(O—C$_6$H$_5$)$_2$ with a benzenesulfonamide of formula III and/or its salt of formula V in the presence of a base, and then treating the N-cyano—O— phenylbenzenesulfonylisourea obtained as an intermediate with an amine of formula R(2)—NH$_2$.

Benzenesulfonamides of formula III as starting compounds for the abovementioned processes for the synthesis of benzenesulfonyl(thio)ureas of formula I can be prepared by or analogously to known methods such as are described in the literature, for example in the standard works such as Houben-Weyl, *Methoden der Organischen Chemie* (Methods of Organic Chemistry), Georg Thieme Verlag, Stuttgart, and *Organic Reactions*, John Wiley & Sons, Inc., New York, and also in the patent documents indicated above, if appropriate with suitable adaptation of the reaction conditions which is familiar to the person skilled in the art. Use can also be made of synthetic variants which are known per se, but not mentioned here in greater detail. In the syntheses, it may also be appropriate to temporarily block functional groups which would react in an undesired manner or give rise to side reactions, by protective groups or to employ them in the form of precursor groups which are converted into the desired groups only later. Strategies of this type are known to the person skilled in the art. Starting substances, if desired, can also be formed in situ in such a way that they are not isolated from the reaction mixture but immediately reacted further.

Thus, for example, p-substituted benzene derivatives of formula IX

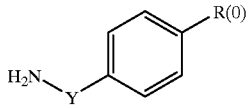

IX in which Y has the abovementioned meanings and R(0), for example, is $(C_1-C_4)$-alkyl, $(C_1-C_4)$-alkoxy, bromine, or nitro, can be reacted with trifluoroacetic anhydride in the presence of pyridine in an inert solvent such as THF to give compounds of formula X

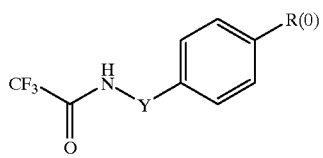

X in which Y and R(0) have the meanings indicated above.

Starting from compounds of formula X in which R(0) is nitro, it is possible by means of a reduction of the nitro group using a reductant such as, for example, $SnCl_2 \times 2\ H_2O$ in an inert solvent such as ethyl acetate, diazotization of the resulting amino group, and subsequent reaction of the intermediate diazo compound by processes known per se, such as are described, for example, in Larock, *Comprehensive Organic Transformations*, VCH, (1989), for example by reaction with potassium iodide for the preparation of the iodo compounds, to obtain the corresponding p-halo-substituted compounds of formula Xl

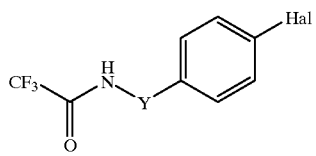

XI in which Y has the meanings indicated above and Hal is halogen.

Compounds of formula XI and compounds of formula X in which R(0) is $(C_1-C_4)$-alkyl, $(C_1-C_4)$-alkoxy, or bromine, which are summarily designated as compounds of formula XII

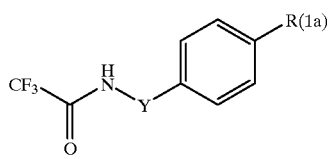

XII in which Y has the meanings indicated above, and R(1a) is $(C_1-C_4)$-alkyl, $(C_1-C_4)$-alkoxy, or halogen, can be converted in a manner known per se into the benzenesulfonamides of formula XIII

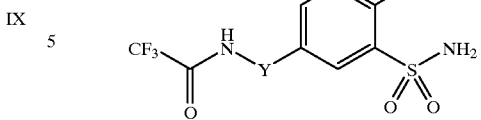

XIII in which Y and R(1a) have the meanings mentioned. Sulfonamides of formula XIII can be prepared from compounds of formula XII in at least one step. In particular, processes are preferred in which acylamines of formula XII are first converted into 2,5-substituted benzenesulfonic acids or their derivatives such as, for example, sulfonyl halides, by electrophilic reagents in the presence or absence of inert solvents at temperatures of −20° C. to 120° C., preferably of 0° C. to 100° C. For this, it is possible to carry out, for example, sulfonations with sulfuric acids or oleum, halosulfonations with halosulfonic acids such as chlorosulfonic acid, reactions with sulfuryl halides in the presence of anhydrous metal halides, or reactions with thionyl halides in the presence of anhydrous metal halides with subsequent oxidations carried out in a known manner to give sulfonyl chlorides. If sulfonic acids are the primary reaction products, these can either be converted into sulfonyl acid halides directly in a manner known per se by means of acid halides such as, for example, phosphorus trihalides, phosphorus pentahalides, thionyl halides, or oxalyl halides, or after treatment with amines such as, for example, triethylamine or pyridine, or alkali metal or alkaline earth metal hydroxides or reagents which form these basic compounds in situ. Sulfonic acid derivatives are converted into sulfonamides of formula XIII in a manner known from the literature. Preferably, sulfonyl acid chlorides are reacted with aqueous ammonia in an inert solvent such as, for example, acetone at temperatures of 0° C. to 100° C.

For the preparation of compounds of formula I in which R(1) is $(C_1-C_4)$-alkyl, $(C_1-C_4)$-alkoxy, or halogen, compounds of formula XIII can be converted by treatment with an acid such as, for example, hydrochloric acid or sulfuric acid, if appropriate with addition of a polar organic solvent such as methanol or ethanol, at temperatures of 0° C. up to the boiling point of the solvent, into compounds of formula XIV

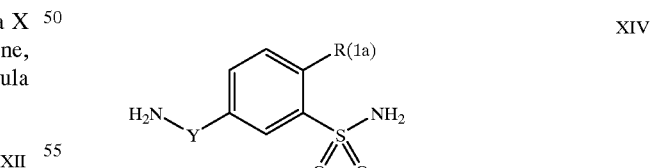

XIV in which R(1a) is $(C_1-C_4)$-alkyl, $(C_1-C_4)$-alkoxy, or halogen, and Y has the meanings indicated above. For the preparation of compounds of formula I in which R(1) denotes the other abovementioned residues, the sulfonamide group in suitable compounds of formula XIII can first be temporarily protected by conversion into the N-(N,N-dimethylaminomethylene)sulfonamide group. For example, starting from compounds of formula XIII, dimethylaminomethylene compounds of formula XV

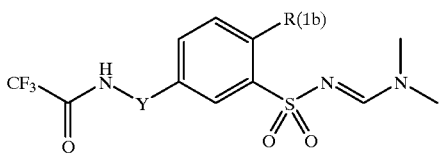

XV in which Y has the meanings mentioned, and R(1b) is (C₁–C₄)-alkoxy, bromine, or iodine, can be prepared by reacting compounds of formula XIII, for example, with N,N-dimethylformamide dimethyl acetal or reacting with N,N-dimethylformamide in the presence of dehydrating agents such as thionyl chloride, phosphorus oxychloride, or phosphorus pentachloride.

Compounds of formula XV in which R(1b) is (C₁–C₄)-alkoxy can then be converted by ether cleavage into phenols of formula XVI

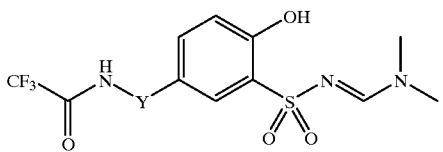

XVI in which Y is as defined above. This ether cleavage is carried out, for example, by treatment of methoxy compounds of formula XV with acids or with Lewis acids such as boron trifluoride, boron trichloride, boron tribromide, or aluminum trichloride, or their etherates, preferably with boron tribromide in an inert solvent such as, for example, methylene chloride.

Phenols of formula XVI obtained can be converted into compounds of formula XVII

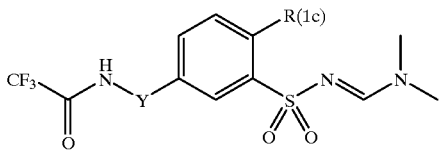

XVII in which Y has the abovementioned meanings and R(1c) is one of the residues —O—(C₁–C₄)-alkyl-E(1)—(C₁–C₄)-alkyl-D(1), —O—(C₁–C₄)-alkyl which is substituted by an oxygen heterocycle, —O—(C₂–C₄)-alkenyl, —O—(C₁–C₄)-alkyl-phenyl, or —O-phenyl. This conversion is carried out by means of an O-alkylation of phenols of formula XVI using appropriately substituted halogen compounds, for example iodides or bromides, or appropriately substituted sulfonic acid esters such as mesylates, tosylates, or trifluoromethylsulfonates. Thus, for example, with 2-bromoethyl methyl ether or benzyl bromide, compounds of formula I are obtained in which R(1) is 2-methoxyethoxy- or benzyloxy. The O-alkylation is in general carried out in the presence of a base in an inert solvent at temperatures of 0° C. up to the boiling point of the solvent by processes known per se. The preparation of compounds of formula XVII in which R(1c) is —O-phenyl is carried out by means of an O-arylation of phenols of formula XVI using phenylboronic acids, for example phenylboronic acid or substituted phenylboronic acids such as 4-methoxyphenylboronic acid, in the presence of copper catalysts, for example copper(II) acetate, for example analogously to the reactions described in *Tetrahedron Lett.* 39 (1998) 2937.

Starting from compounds of formula XV in which R(1b) is bromine or iodine, compounds of formula XVIII

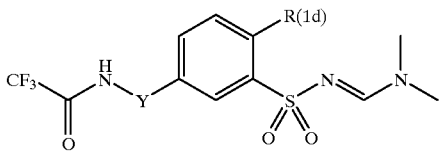

XVIII can be obtained in which Y has the meanings indicated, and R(1d) is one of the residues (C₁–C₄)-alkyl, phenyl, (C₂–C₅)-alkenyl, (C₂–C₅)-alkynyl, heteroaryl, —S(O)ₘ-phenyl, or —S(O)ₘ—(C₁–C₄)-alkyl. This conversion into compounds of formula XVIII is carried out by means of palladium-catalyzed Suzuki coupling with arylboronic acids, for example phenylboronic acid, 4-methoxyphenylboronic acid, or 4-methylthiophenylboronic acid, or heteroarylboronic acids, for example thienylboronic acid, or by Stille coupling with trialkylstannanes, for example tributylstannylfuran, trimethylstannylpyridine, or ethynyltributylstannane. The Suzuki coupling is carried out in the presence of palladium (II) acetate and triphenylphosphine or tetrakis (triphenylphosphine)palladium and a base such as, for example, cesium carbonate or potassium carbonate; corresponding reactions are described in the literature. The Stille coupling is carried out analogously to literature procedures using bis(triphenylphosphine)palladium(II) chloride as a catalyst. The preparation of suitable stannanes is described, for example, in *Tetrahedron* 49 (1993) 3325. The preparation of compounds of formula XVIII in which R(1d) is alkyl is carried out by Pd(0)-catalyzed Nikishi-Kumada coupling of compounds of formula XV in which R(1b) is iodine with an appropriate organozinc derivative in the presence of 1,1'-bis(diphenylphosphino)ferrocene, palladium(II) acetate, and copper(I) iodide as catalysts in an inert solvent; corresponding couplings are described, for example, in *Synlett* (1996) 473.

Compounds of formula XVIII in which R(1d) is —S-phenyl or —S-(C₁–C₄)-alkyl can be prepared analogously to literature procedures by means of a copper(I) iodidecatalyzed nucleophilic substitution reaction from compounds of formula XV in which R(1b) is iodine, using the sodium salt of the corresponding mercaptan. The thioether group thus introduced, and also a thioether group in another position of the molecule of formula I, can be oxidized to the sulfoxide group or to the sulfone group by standard processes, for example using a peracid such as m-chloroperbenzoic acid.

The subsequent removal of the dimethylaminomethylene group and/or the trifluoroacetyl group functioning as a sulfonamide protective group or amino protective group, respectively, from compounds of formulae XVII and XVIII then leads to the corresponding compounds having an H₂N—Y group and H₂N—SO₂ group, which are represented together with compounds of formula XIV by formula XIX

XIX

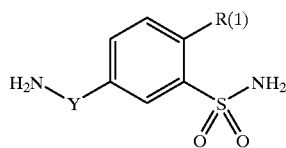

in which Y and R(1) have the meanings indicated above for formula I. This removal of the protective groups can be carried out either under basic or under acidic conditions. Preferably, it is carried out by treatment of compounds of formulae XVII and XVIII in a suitable solvent, for example an alcohol, with acids such as, for example, hydrochloric acid.

Benzenesulfonamides of formula XIX are then reacted with cinnamic acid derivatives to give cinnamoylaminoalkyl-substituted benzenesulfonamides of formula III. In general, this acylation is carried out by first converting the appropriate cinnamic acid into a reactive derivative, for example by reaction of the cinnamic acid with carbonylbisimidazole in an inert solvent such as, for example, THF, dioxane, or DMF, and subsequent reaction with the amine of formula XIX, if appropriate in the presence of a base such as triethylamine or pyridine. Reactive cinnamic acid derivatives which can be used, for example, are also cinnamic acid halides or cinnamic anhydrides. The reactions are in this case preferably carried out at temperatures from 0° C. up to the boiling point of the solvent chosen, particularly preferably at room temperature. The acylation of amines of formula XIX with cinnamic acids can also be carried out, for example, in the presence of condensing agents such as, for example, N,N'-dicyclohexylcarbodiimide, O-((cyano-(ethoxycarbonyl)methylene)amino)-1,1,3,3-tetramethyluronium tetrafluoroborate (TOTU), or 1-benzotriazolyloxytripyrrolidinophosphonium hexafluorophosphate (PyBOP).

The steps for the preparation of compounds of formula I described can also be carried out in other sequences. Depending on the substituents to be introduced in the individual steps, one or the other variants can be more advantageous. Thus, for example, the preparation of compounds of formula III in which R(1) is one of the residues ($C_1$–$C_4$)-alkyl, phenyl, ($C_2$–$C_5$)-alkenyl, ($C_2$–$C_5$)-alkynyl, heteroaryl, —S(O)$_m$-phenyl, or —S(O)$_m$—($C_1$–$C_4$)-alkyl, can also be carried out in such a way that a compound of formula XIV in which R(1a) is iodine or bromine is first converted, by means of the coupling with a cinnamic acid derivative described above and temporary protection of the sulfonamide group, into a compound of formula XX

XX

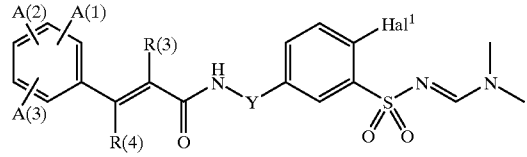

in which A(1), A(2), A(3), R(3), R(4), and Y are defined as for formula I and Hal¹ is iodine or bromine. Starting from the compound of formula XX, it is then possible by means of the Suzuki, Stille, or Nikishi-Kumada couplings described above with the appropriate coupling components mentioned above to obtain compounds of formula XXI

XXI

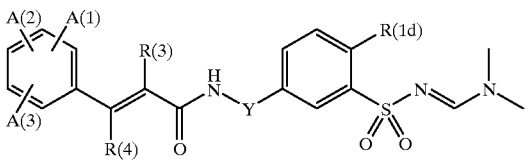

in which A(1), A(2), A(3), R(1d), R(3), R(4), and Y have the meanings indicated above. Compounds of formula XXI can then be converted into compounds of formula III by removal of the sulfonamide protective group according to the process described above.

Compounds of formula I inhibit ATP-sensitive potassium channels and affect the action potential of cells, in particular of cardiac muscle cells. In particular, they have a normalizing action on a disturbed action potential, as is present, for example, in ischemias, and are suitable, for example, for the treatment and prophylaxis of disorders of the cardiovascular system, in particular of arrhythmias and their sequelae, for example of ventricular fibrillation. The activity of compounds of formula I can be demonstrated, for example, in the model described below in which the action potential duration is determined on the papillary muscle of the guinea pig.

In addition to their action on ATP-sensitive potassium channels in the heart muscle cell, compounds of formula I also have an action on the peripheral and/or the central autonomic nervous system. In particular, they affect ATP-sensitive potassium channels of the vagal nervous system and have a stimulating action on the vagal nervous system, in particular a stimulating action on the vagal nervous system of the heart by inhibition of ATP-sensitive potassium channels in the cardiac nerve.

In the ideal case, an optimum cooperation, adapted to the particular situation, exists between the vagal (or parasympathetic) nervous system (=depressing nervous system) and the sympathetic nervous system (=stimulating nervous system). In the case of disease, however, this cooperation can be disturbed and a dysfunction of the autonomic nervous system can be present, that is an imbalance can exist between the activity of the vagal nervous system and the activity of the sympathetic nervous system. Sympathovagal imbalance is understood in general as meaning an overactivity or hyperfunction of the sympathetic (=stimulating) nervous system and/or an impaired function or hypofunction of the vagal (=depressing) nervous system, where the two parts of the nervous system can mutually influence each other. In particular, it is known that a hypofunction of the vagal system can result in a hyperfunction of the sympathetic system. For the avoidance of damage to cells or organs of the body by overshooting biological or biochemical processes which are stimulated by too high an activity of the sympathetic nervous system, it is therefore attempted in such cases to balance out a sympathovagal imbalance, for example to restore the normal vagal activity by treating a vagal dysfunction or hypofunction.

Examples of diseases in which elimination of a harmful sympathovagal imbalance by treatment of a vagal dysfunction is possible are organic heart diseases, for example coronary heart disease, cardiac insufficiency, and cardiomyopathies. Damages to health which result from an imbalance of the autonomic nervous system when the dysfunction relates to the heart are, for example, weakening of the myocardial contractile force and fatal cardiac arrhythmias. The significance of the autonomic nervous system for sudden cardiac death in heart disease was described, for example, by P. J. Schwartz ("The ATRAMI prospective study: implications for risk stratification after myocardial infarction," Cardiac Electrophysiology Review 2 (1998) 38–40) or T. Kinugawa et al. ("Altered vagal and sympathetic control of heart rate in left ventricular dysfunction and heart failure," Am. J. Physiol. 37 (1995) R310–R316). Experimental investigations with electrical stimulation of the cardiac vagus nerve or stimulating analogs of the vagal transmitter acetylcholine, for example carbachol, confirm the protective action of a vagal activation against fatal cardiac arrhythmias (see, for example, E. Vanoli et al., "Vagal stimulation and prevention of sudden death in conscious dogs with a healed myocardial infarction," Circ. Res. 68(5) (1991) 1471–1481).

A sympathovagal imbalance, however, can also occur, for example, as a result of a metabolic disorder, for example diabetes mellitus (see, for example, A. J. Burger et al., "Short- and long-term reproducibility of heart rate variability in patients with long-standing type I diabetes mellitus," Am. J. Cardiol. 80 (1997) 1198–1202). A hypofunction of the vagal system can also temporarily occur, for example in the case of oxygen deficiency, for example oxygen deficiency of the heart, which leads to an undersecretion of vagal neurotransmitters, for example of acetylcholine.

On account of the surprising ability of compounds of formula I to abolish a hypofunction of the vagal system or to restore the normal vagal activity, these compounds offer an efficient possibility of decreasing, eliminating, or preventing dysfunctions of the autonomic nervous system, in particular in the heart, and its consequences such as, for example, the disease conditions mentioned. The efficacy of compounds of formula I in the abolition of dysfunctions of the autonomic nervous system, in particular of a vagal dysfunction of the heart, can be demonstrated, for example, in the model of chloroform-induced ventricular fibrillation in the mouse described below.

The above and the following statements regarding the biological action on ATP-sensitive potassium channels in the heart and on the autonomic nervous system and the uses of compounds of formula I do not only apply to the compounds defined above which are per se a subject of the present invention, but also to compounds of formula I in which, simultaneously, X is oxygen, Z is NH, R(1) is halogen, $(C_1-C_4)$-alkyl, or —O—$(C_1-C_4)$-alkyl, and R(2) is $(C_2-C_6)$-alkyl or $(C_5-C_7)$-cycloalkyl, or a physiologically tolerable salt or prodrug thereof, that is also to compounds which are excluded by the disclaimer in the above definition of the compounds but which likewise surprisingly have an action on the autonomic nervous system, in particular on the heart, and can abolish vagal dysfunctions. If not stated otherwise, in the above and the following statements regarding their biological action and use, compounds of formula I are expressly to be understood as including also the compounds excluded above by the disclaimer. The above explanations with respect to the compounds per se, for example with respect to preferred meanings of residues, correspondingly apply to all compounds of formula I as understood here. As particularly preferred groups of compounds with respect to the biological action and the uses, moreover those compounds of formula I, including compounds in which, at the same time, X is oxygen, Z is NH, R(1) is halogen, $(C_1-C_4)$-alkyl, or —O—$(C_1-C_4)$-alkyl, and R(2) is $(C_2-C_6)$-alkyl or $(C_5-C_7)$-cycloalkyl, or a physiologically tolerable salt thereof, may be mentioned here in which R(2) is $(C_1-C_3)$-alkyl, in particular methyl, and/or X is sulfur.

Compounds of formula I, or a physiologically tolerable salt thereof, can be used as pharmaceuticals on their own, in mixtures with one another, or in the form of pharmaceutical preparations in animals, preferably in mammals, and in particular in humans. Mammals in which compounds of formula I can be used or tested are, for example, monkeys, dogs, mice, rats, rabbits, guinea pigs, cats, and larger farm animals such as, for example, cattle and pigs. The invention therefore also relates to compounds of formula I where the compounds are excluded in which, simultaneously, X is oxygen, Z is NH, R(1) is halogen, $(C_1-C_4)$-alkyl, or —O—$(C_1-C_4)$-alkyl, and R(2) is $(C_2-C_6)$-alkyl or $(C_5-C_7)$-cycloalkyl, or a physiologically tolerable salt or a prodrug thereof for use as pharmaceuticals. The invention also relates to pharmaceutical preparations (or pharmaceutical compositions) which contain an efficacious dose of at least one compound of formula I where the compounds are excluded in which, simultaneously, X is oxygen, Z is NH, R(1) is halogen, $(C_1-C_4)$-alkyl, or —O—$(C_1-C_4)$-alkyl, and R(2) is $(C_2-C_6)$-alkyl or $(C_5-C_7)$-cycloalkyl—and/or a physiologically tolerable salt and/or a prodrug thereof as an active constituent and at least one pharmaceutically tolerable carrier, that is at least one pharmaceutically innocuous vehicle and/or additive.

The pharmaceutical preparations can be intended for enteral or parenteral use and normally contain about 0.5 to about 90 percent by weight of the compound of formula I and/or a physiologically tolerable salt thereof. The amount of active compound of formula I and/or a physiologically tolerable salt thereof in the pharmaceutical preparations is in general about 0.2 to about 1000 mg, preferably about 1 to about 500 mg. The pharmaceutical preparations can be produced in a manner known per se. For this, compounds of formula I and/or a physiologically tolerable salt thereof are mixed together with at least one solid or liquid vehicle and/or excipient and, if desired, in combination with at least one other pharmaceutical, for example cardiovascular-active pharmaceuticals such as, for example, calcium antagonists, ACE inhibitors, or β-blockers, and brought into a suitable dose form and administration form, which can then be used as a pharmaceutical in human medicine or veterinary medicine.

Suitable vehicles are organic and inorganic substances which are suitable, for example, for enteral (for example oral or rectal) administration or for parenteral administration (for example intravenous, intramuscular, or subcutaneous injection or infusion) or for topical or percutaneous application, and do not react with compounds of formula I in an undesired manner. Examples which may be mentioned are water, vegetable oils, waxes, alcohols such as ethanol, propanediol, or benzyl alcohols, glycerol, polyols, polyethylene glycols, polypropylene glycols, glycerol triacetate, gelatin, carbohydrates such as lactose or starch, stearic acid and its salts such as magnesium stearate, talc, lanolin, petroleum jelly, or mixtures of vehicles, for example mixtures of water with at least one organic solvent, such as mixtures of water with alcohols. For oral and rectal administration, in particular pharmaceutical forms such as tablets, film-coated tablets, sugar-coated tablets, granules, hard and soft gelatin capsules, suppositories, solutions, preferably oily, alcoholic, or aqueous solutions, syrups, juices, or drops, furthermore suspensions or emulsions, are used. For topical administration, in particular ointments, creams, pastes, lotions, gels, sprays, foams, aerosols, solutions, or powders are used. Solvents for solutions that can be used are, for example, water or alcohols such as ethanol, isopropanol, or 1,2-propanediol, or their mixtures with one another or with water. Further possible pharmaceutical forms are, for example, also implants. Compounds of formula I or a physiologically tolerable salt thereof can also be lyophilized and the lyophilizates obtained used, for example, for the production of injection preparations. Liposomal preparations are also possible, in particular for topical application. Examples of excipients (or additives) which can be present in the pharmaceutical preparations and which may be mentioned are lubricants, preservatives, thickeners, stabilizing agents, disintegrants, wetting agents, agents for achieving a depot effect, emulsifiers, salts (for example for affecting the osmotic pressure), buffer substances, colorants, flavorings, and aromatizers. The pharmaceutical preparations, if desired, can also contain at least one further active compound and/or, for example, at least one vitamin.

On account of their ability to inhibit ATP-sensitive potassium channels, in particular in the heart, and/or to decrease or to eliminate an inadequate function of the vagal nervous system and thereby a vagal dysfunction or a dysfunction of the autonomic nervous system, in particular in the heart, compounds of formula I or a physiologically tolerable salt or prodrug thereof are valuable agents for therapy and prophylaxis which are suitable not only as antiarrhythmics and for the control and prevention of the sequelae of arrhythmias, but also for treatment and prophylaxis in other heart diseases or disorders of the cardiovascular system. Examples of diseases of this type which may be mentioned are cardiac insufficiency, cardiomyopathies, cardiac hypertrophy, coronary heart disease, angina pectoris, ischemias, vagal dysfunction of the heart, or, for example, vagal dysfunction of the heart in diabetes mellitus. Compounds of formula I can be generally employed in the therapy or prophylaxis of diseases which are associated with a dysfunction of the autonomic nervous system or a hypofunction or dysfunction of the vagal nervous system, in particular in the heart, or are caused by a dysfunction of this type or for whose therapy or prophylaxis an increase or normalization of the activity of the vagal nervous system is desired. Compounds of formula I can also be employed in dysfunctions of the autonomic nervous system, in particular a vagal dysfunction in the heart, which occur as a result of a metabolic disorder such as, for example, diabetes mellitus.

Above all, compounds of formula I are used as antiarrhythmics for the treatment of cardiac arrhythmias of very different origins and especially for the prevention of sudden cardiac death due to arrhythmia. Examples of arrhythmic disorders of the heart are supraventricular arrhythmias such as, for example, atrial tachycardia, atrial flutter, or paroxysmal supraventricular arrhythmias, or ventricular arrhythmias such as ventricular extrasystoles, but in particular life-threatening ventricular tachycardia or the particularly dangerous ventricular fibrillation. They are particularly suitable for those cases where arrhythmias are a result of a constriction of a coronary vessel such as occur, for example, in angina pectoris or during acute cardiac infarct or as a chronic result of a cardiac infarct. They are therefore particularly suitable in postinfarct patients for the prevention of sudden cardiac death. Further syndromes in which arrhythmias of this type and/or sudden cardiac death due to arrhythmia play a role are, for example, cardiac insufficiency or cardiac hypertrophy as a result of chronically raised blood pressure.

Moreover, compounds of formula I are able to positively affect decreased contractility of the heart and a weakened myocardial contractile force. This can be a disease-related decline in cardiac contractility, such as, for example, in cardiac insufficiency, but also acute cases such as heart failure as an effect of shock. Generally, compounds of formula I or a physiologically tolerable salt thereof are suitable for improving cardiac function. Especially in a heart transplantation, under the influence of compounds of formula I the heart can also resume its capability faster and more reliably after the operation has taken place. The same applies to operations on the heart which necessitate temporarily stopping cardiac activity by means of cardioplegic solutions.

By virtue of the fact that compounds of formula I, in addition to their direct cardiac action, that is the effect on the action potential of the cardiac muscle cells, also have an indirect action on the nervous system of the heart or the parts of the nervous system acting on the heart, they can decrease or prevent the undesired sequelae on the heart starting from the nervous system or mediated by the nervous system in the respective disease state present. Further damage to health such as a weakening of the myocardial contractile force or in some cases fatal cardiac arrhythmias such as ventricular fibrillation can thereby be reduced or avoided. Through the elimination or reduction of the dysfunction of the autonomic nervous system, compounds of formula I have the effect that the weakened myocardial contractile force is normalized again and the cardiac arrhythmias which can lead to sudden cardiac death can no longer result. By selection of compounds of formula I having a suitable profile of action with respect to direct cardiac action (=direct effect on the action potential of the cardiac muscle cells and on account of this direct effect on the contractile force and direct antiarrhythmic action) on the one hand and the action on the cardiac nerves on the other hand, it is possible in a particularly efficient manner with the aid of compounds of formula I to favorably influence heart diseases. Depending on the syndrome present, it can also be advantageous in this case to employ compounds of formula I which only have a relatively low direct cardiac effect and owing to this, for example, only have a relatively low direct effect on the contractile force of the heart or the formation of arrhythmias, but can improve or normalize the myocardial contractile force or the heart rhythm via the effect of the autonomic nervous system.

The present invention therefore also relates to the use of compounds of formula I —including compounds in which, at the same time, X is oxygen, Z is NH, R(1) is halogen, $(C_1-C_4)$-alkyl, or —O—$(C_1-C_4)$-alkyl, and R(2) is $(C_2-C_6)$-alkyl or $(C_5-C_7)$-cycloalkyl—and/or a physiologically tolerable salt and/or prodrug thereof, for the therapy or prophylaxis of the syndromes mentioned, and the use for the production of pharmaceuticals for the therapy or prophylaxis of the syndromes mentioned. Of compounds of formula I in which, simultaneously, X is oxygen, Z is NH, R(1) is halogen, $(C_1-C_4)$-alkyl, or —O—$(C_1-C_4)$-alkyl, and R(2) is $(C_2-C_6)$-alkyl or $(C_5-C_7)$-cycloalkyl, preferred compounds for the therapy or prophylaxis of the syndromes mentioned and for the production of pharmaceuticals for the therapy or prophylaxis of the syndromes mentioned are those compounds which only have a slight effect on the blood sugar level.

The dosage of compounds of formula I or a physiologically tolerable salt thereof depends, as is customary, on the circumstances of the respective individual case, and is adjusted by the person skilled in the art according to the customary rules and procedures. It depends, for example, on the compound of formula I administered, its potency and duration of action, on the nature and severity of the individual syndrome, on the sex, age, weight, and the individual responsiveness of the human or animal to be treated, on whether treatment is acute or prophylactic, or whether, in addition to compounds of formula I, further active compounds are administered. Normally, in the case of administration to an adult weighing about 75 kg, a dose is needed which is about 0.1 mg to about 100 mg per kg per day, preferably about 1 mg to about 10 mg per kg per day (in each case in mg per kg of body weight). The daily dose can be administered in the form of an oral or parenteral individual dose or can be divided into several, for example two, three, or four, individual doses. The administration can also be carried out continuously. In particular, if acute cases of cardiac arrhythmias are treated, for example in an intensive care unit, parenteral administration, for example by injection or by intravenous continuous infusion, can be advantageous. A preferred dose range in critical situations is then about 1 mg to about 100 mg per kg of body weight per day. If appropriate, depending on individual behavior, it may be necessary to deviate upwards or downwards from the doses indicated.

Apart from as a pharmaceutical active compound in human medicine and veterinary medicine, compounds of formula I can also be employed, for example, as auxiliaries for biochemical investigations or as a scientific tool if a respective effect on ion channels is intended, or for the isolation or characterization of potassium channels. They can furthermore be used for diagnostic purposes, for example in in-vitro diagnoses of cell samples or tissue samples. Compounds of formula I or a salt thereof can further be used as chemical intermediates, for example for the preparation of further pharmaceutical active compounds.

A subject of the present invention are also certain cinnamoylaminoalkyl-substituted benzenesulfonylureas per se which are excluded by the disclaimer from the above-defined compounds of formula I which are per se a subject of the present invention, but which are not specifically disclosed in the prior art and which are a selection from compounds disclosed in general form in the prior art. These are compounds of formula If

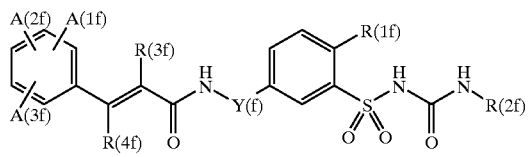

IF in which:
Y(f) is —(CR(5f)$_2$)$_{n(f)}$—;
the residues A(1f), A(2f), and A(3f), which are independent of one another and can be identical or different, are hydrogen, halogen, (C$_1$–C$_4$)-alkyl, (C$_1$–C$_4$)-alkoxy, methylenedioxy, formyl, or trifluoromethyl;
R(1f) is —O—(C$_1$–C$_4$)-alkyl;
R(2f) is (C$_2$–C$_6$)-alkyl or (C$_5$–C$_7$)-cycloalkyl; the residues R(3f) and R(4f), which are independent of one another and can be identical or different, are hydrogen or (C$_1$–C$_4$)-alkyl;
the residues R(5f), which are independent of one another and can be identical or different, are hydrogen or (C$_1$–C$_3$)-alkyl;
n(f) is 1, 2, 3, or 4;
in any stereoisomeric form or mixture thereof in any ratio, or a physiologically tolerable salt thereof.

Like compounds of formula I, compounds of formula If also inhibit—as already explained above—ATP-sensitive potassium channels, in particular in the heart, and are able to reduce or repair a dysfunction of the autonomic nervous system or a hypofunction or dysfunction of the vagal nervous system, in particular in the heart. All above details of compounds of formula I apply correspondingly to compounds of formula If. In compounds of formula If, Y(f) is preferably the residue —CH$_2$—CH$_2$—. The residues A(1), A(2f), and A(3f), which are independent of one another and can be identical or different, are preferably hydrogen, halogen, (C$_1$–C$_4$)-alkyl, (C$_1$–C$_4$)-alkoxy, or trifluoromethyl, in particular hydrogen, methyl, chlorine, fluorine, methoxy, ethoxy, or trifluoromethyl. The further statements with respect to preferred meanings of the residues A(1), A(2), and A(3) given above apply correspondingly to A(1f), A(2f), and A(3f). R(1f) is preferably methoxy or ethoxy, in particular methoxy. R(2f) is preferably (C$_2$–C$_3$)-alkyl or cyclohexyl, in particular ethyl, isopropyl, or cyclohexyl. R(3f) and R(4f) are preferably hydrogen. The present invention also relates to compounds of formula If or a physiologically tolerable salt or prodrug thereof for use as pharmaceuticals, and also pharmaceutical preparations which contain an efficacious amount of at least one compound of formula If and/or a physiologically tolerable salt and/or a prodrug thereof and a pharmaceutically tolerable carrier. Again, the above statements apply correspondingly to these pharmaceutical preparations.

The invention is illustrated by the examples below, without being restricted to these.

| Abbreviations | |
| --- | --- |
| DCI | desorption chemical ionization |
| DCM | dichloromethane |
| EA | ethyl acetate |
| ESI | electron spray ionization |
| FAB | fast atom bombardment |
| M.p. | melting point |
| h | hour(s) |
| min | minute(s) |
| MS | mass spectrum |
| RT | room temperature |

EXAMPLE 1

1-(5-(2-(2,4-Dimethoxycinnamoylamino)ethyl)-2-methoxyphenysulfonyl)-3-methylthiourea

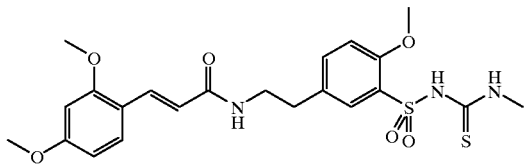

a) 2,2,2-Trifluoro-N-(2-(4-methoxyphenyl)ethyl)acetamide
32.2 ml (0.23 mol) of trifluoroacetic anhyd ride were added dropwise to a solution of 22.3 ml (0.15 mol) of 2-(4-methoxyphenyl)ethylamine and 24.7 ml (0.23 mol) of pyridine in 125 ml of absolute THF cooled to 5° C., and the resulting solution was stirred at RT for 3 h. The reaction solution was then poured onto 750 ml of ice, and the precipitate deposited was filtered off with suction and dried at 40° C. under high vacuum. 36.3 g of the title compound resulted in the form of a beige solid.

M.p.: 74–77° C.; $R_f$ (SiO$_2$, EA/toluene 1:4)=0.62. MS (ESI): m/e=248 (M+H)$^+$ b) 2-Methoxy-5-(2-(2,2,2-trifluoroacetamido)ethyl) benzenesulfonamide 36.3 g (0.15 mol) of the compound from Example 1a) were added in portions to 200 ml of chlorosulfonic acid and the resulting mixture was stirred at RT for 2 h. The reaction solution was then added dropwise to about 1.5 l of ice and the precipitate deposited was filtered off with suction. The precipitate obtained was dissolved in 100 ml of acetone, and the solution was treated with 250 ml of conc. ammonia solution with ice-cooling and stirred for 45 min. The reaction solution was then poured onto about 800 ml of ice. The precipitate deposited was filtered off with suction and dried under high vacuum. Yield: 30.4 g of the title compound in the form of a pale yellow solid.

M.p.: 160–161° C.; $R_f$ (SiO$_2$, EA$^{/heptane}$ 4:1)=0.51. MS (DCI): m/e=327 (M+H)$^+$ c) 5-(2-Aminoethyl)-2-methoxybenzenesulfonamide A solution of 30.3 g (93.0 mmol) of the compound from Example 1b) in 130 ml of 2 N hydrochloric acid was heated to reflux for 12 h. The precipitate deposited was filtered off with suction and dissolved in 70 ml of water, and the pH of the resulting solution was adjusted to about 10 by addition of 2 N sodium hydroxide solution. It was briefly warmed to 100° C. The solution was then cooled in an ice bath and the precipitate deposited was filtered off with suction and dried under high vacuum. Yield: 13.7 g of the title compound in the form of a beige solid.

M.p.: 180–181° C.; $R_f$ (SiO$_2$, EA/heptane 4:1)=0.02. MS (ESI): m/e=231 (M+H)$^+$ d) 5-(2-(2,4-Dimethoxycinnamoylamino)ethyl)-2-methoxybenzenesulfonamide A solution of 500 mg (2.17 mmol) of the compound from Example 1c), 452 mg (2.17 mmol) of trans-2,4-dimethoxycinnamic acid, 752 mg (2.17 mmol) of TOTU, and 382 μl (2.17 mmol) of N-ethyldiisopropylamine in 50 ml of absolute DMF was stirred at RT for 2 h. The reaction solution was concentrated and the residue was taken up in DCM/water. The organic phase was separated off, the aqueous phase was extracted twice with DCM, and the combined organic phases were dried over Na$_2$SO$_4$. The oily residue remaining after stripping off the solvent was purified by chromatography on SiO$_2$ using DCM/EA (2:1) as an eluent. The product-containing fractions were combined, the solvent was stripped off, and the crystalline residue which remained was triturated in a little EA. The precipitate was filtered off and dried under high vacuum. Yield: 606 mg of the title compound in the form of a white solid.

M.p.: 183° C.; $R_f$ (SiO$_2$, EA/heptane 4:1) 0.13. MS (DCI): m/e=421 (M+H)$^+$ e) 1 -(5-(2-(2,4-Dimethoxycinnamoylamino)ethyl)-2-methoxyphenylsulfonyl)-3-methylthiourea A solution of 600 mg (1.43 mmol) of the compound from Example 1d) and 192 mg (1.71 mmol) of potassium tert-butoxide in 12 ml of absolute DMF was stirred at RT for 15 min. 1.57 ml (1.57 mmol) of a 1-molar solution of methyl isothiocyanate in absolute DMF were added and the resulting solution was stirred at 80° C. for 1 h. The reaction solution was then poured onto 80 ml of 1 N hydrochloric acid, and the precipitate deposited was filtered off with suction and washed several times with water. Drying of the precipitate under high vacuum yielded 626 mg of the title compound in the form of a pale yellow-colored, amorphous solid.

$R_f$ (SiO$_2$, EA/heptane 10:1)=0.52. MS (DCI): m/e=494 (M+H)$^+$

EXAMPLE 2

1-(5-(2-(2,4-Dimethoxycinnamoylamino)ethyl)-2-methoxyphenylsulfonyl)-3-methylurea

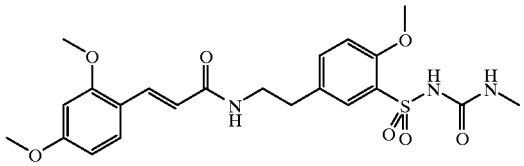

80 mg (0.16 mmol) of the compound from Example 1) were dissolved in 1 ml of 1 N sodium hydroxide solution. 150 μl of a 35% strength aqueous H$_2$O$_2$ solution were added and the resulting solution was heated on a water bath for 30 min. The pH of the solution was then adjusted to 2 by addition of 2 N hydrochloric acid, and the precipitate deposited was washed with a little water and finally dried under high vacuum. 63 mg of the title compound resulted as a white solid.

M.p.: 210° C.; $R_f$ (SiO$_2$, EA/heptane 4:1)=0.06. MS (DCI): m/e=478 (M+H)$^+$

EXAMPLE 3

1-(5-(2-(2,4-Dimethoxycinnamoylamino)ethyl)-2-methoxyphenylsulfonyl)-3-ethylthiourea

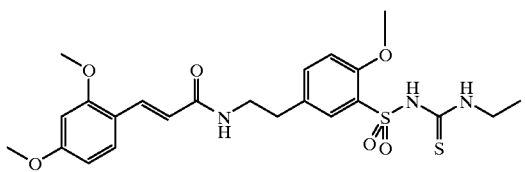

The preparation was carried out according to the process described in Example 1e), ethyl isothiocyanate being used instead of methyl isothiocyanate. In this case, there resulted from 150 mg (0.36 mmol) of the compound from Example 1d) and 36.1 μl (0.39 mmol) of ethyl isothiocyanate 161 mg of the title compound in the form of a pale yellow solid.

M.p.: 90° C. (softening). $R_f$ (SiO$_2$, EA/heptane 10:1)= 0.42. MS (ESI): m/e=508 (M+H)$^+$

EXAMPLE 4

1-(5-(2-(2,4-Dimethoxycinnamoylamino)ethyl)-2-methoxyphenylsulfonyl)-3-ethylurea

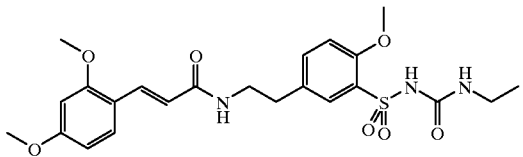

The preparation was carried out according to the process described in Example 2). From 80 mg (0.16 mmol) of the compound from Example 3), there resulted 69 mg of the title compound in the form of a white solid.

M.p.: 96° C. (softening). $R_f$ (SiO$_2$, EA/heptane 10:1)= 0.14. MS (FAB): m/e=492 (M+H)$^+$

EXAMPLE 5

1-(5-(2-(2,4-Dimethylcinnamoylamino)ethyl)-2-methoxyphenylsulfonyl)-3-methylthiourea

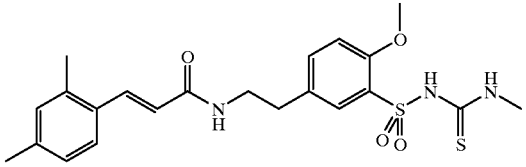

a) 5-(2-(2,4-Dimethylcinnamoylamino)ethyl)-2-methoxybenzenesulfonamide 341 mg (1.94 mmol) of 2,4-dimethylcinnamic acid and 339 mg (2.1 mmol) of carbonylbisimidazole were dissolved in 15 ml of absolute THF. After stirring at RT for 2 h, 500 mg (2.17 mmol) of the compound from Example 1c) and 870 μl of triethylamine were added to this solution. It was stirred at RT for 12 h and the reaction mixture was then poured onto 40 ml of 1 N HCl solution. The precipitate deposited was filtered off with suction, washed with water, and then dried in vacuo. 610 mg of the title compound were obtained in the form of a white solid.

M.p.: 202° C.; $R_f$ (SiO$_2$, EA/heptane 4:1)=0.25. MS (ESI): m/e=389 (M+H)$^+$ b) 1-(5-(2-(2,4-Dimethylcinnamoylamino)ethyl)-2-methoxyphenylsulfonyl)-3-methylthiourea The preparation was carried out according to the process described in Example 1e). In this case, there resulted from 604 mg (1.56 mmol) of the compound from Example 5a) and 1.7 ml (1.71 mmol) of methyl isothiocyanate 580 mg of the title compound in the form of a white solid.

M.p.: 190–192° C.; $R_f$ (SiO$_2$, EA/heptane 6:1)=0.47. MS (ESI): m/e=462 (M+H)$^+$

EXAMPLE 6

1-(5-(2-(2,4-Dimethylcinnamoylamino)ethyl)-2-methoxyphenylsulfonyl)-3-methylurea

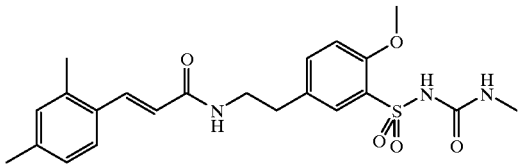

The preparation was carried out according to the process described in Example 2). From 100 mg (0.22 mmol) of the compound from Example 5, there resulted 79 mg of the title compound in the form of a white solid.

M.p.: 227–229° C.; $R_f$ (SiO$_2$, EA/heptane 6:1)=0.10. MS (FAB): m/e=446 (M+H)$^+$

EXAMPLE 7

1-(5-(2-(2,4-Dimethoxycinnamoylamino)ethyl)-2-(2-methoxyethoxy)phenylsulfonyl)-3-methylthiourea

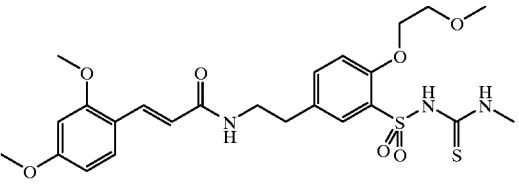

a) N-Dimethylaminomethylene-2-methoxy-5-(2-(2,2,2-trifluoroacetamido)-ethyl)benzenesulfonamide 30.2 g (92.6 mmol) of the compound from Example 1b) were dissolved in 70 ml of absolute DMF, 14.0 ml (105.4 mmol) of dimethylformamide dimethyl acetal were added, and the resulting solution was stirred at RT for 3 h. It was concentrated to dryness and the residue obtained was stirred with 100 ml of water and 100 ml of 5% strength NaHSO$_4$ solution. The crystalline precipitate was filtered off with suction, washed several times with water, and then dried under high vacuum. 29.6 g of the title compound resulted as a white solid.

M.p.: 143–144° C.; $R_f$ (SiO$_2$, EA)=0.25. MS (DCI): m/e=382 (M+H)$^+$ b) N-Dimethylaminomethylene-2-hydroxy-5-(2-(2,2,2-trifluoroacetamido)-ethyl)benzenesulfonamide 100 ml of a 1-molar BBr$_3$ solution in DCM were added dropwise at RT over a period of 40 min to a solution of 29.5 g (77.2 mmol) of the compound from Example 7a) in 450 ml of DCM. After stirring at RT for 5 h, the reaction mixture was treated with 150 ml of methanol and then with about 2 l of diisopropyl ether. The precipitate deposited was filtered off with suction and dried under high vacuum. 32.7 g of the title compound were obtained as the hydrobromide salt in the form of a white solid.

M.p.: 160–161° C.; $R_f$ (SiO$_2$, EA)=0.52. MS (DCI): m/e=368 (M+H)$^+$ c) N-Dimethylaminomethylene-2-(2-methoxyethoxy)-5-(2-(2,2,2-trifluoro-acetamido)ethyl)benzenesulfonamide A solution of 9.1 g (20.3 mmol) of the compound from Example 7b) and 7.1 g (50.8 mmol) of potassium carbonate in 50 ml of absolute DMF were treated with 6.7 ml (71.7 mmol) of 2-bromoethyl methyl ether and the mixture was stirred at 70° C. for 3 h. After adding a further 6.7 ml of 2-bromoethyl methyl ether and stirring at 70° C. for 2 h, the reaction solution was treated with about 300 ml of EA. It was washed with water and saturated NaCl solution, and the organic phase was dried over Na$_2$SO$_4$ and concentrated to dryness. The residual, slightly yellow-colored oil was purified by chromatography on SiO$_2$ using EA as an eluent. After concentrating the product-containing fractions and drying under high vacuum, 7.25 g of the title compound were obtained in the form of a pale yellow solid.

M.p.: 134–136° C.; $R_f$ (SiO$_2$, EA)=0.35. MS (DCI): m/e=426 (M+H)$^+$ d) 5-(2-Aminoethyl)-2-(2-methoxyethoxy)benzenesulfonamide A solution of 7.24 g (17.0 mmol) of the compound from Example 7c) in 100 ml of methanol and 100 ml of half-concentrated hydrochloric acid was heated at reflux for 8 h. About 40 ml of ethanol were then added to the reaction solution and the precipitate deposited was filtered off with suction. The precipitate was washed with cold ethanol and dried under high vacuum. Yield: 4.0 g of the title compound as the hydrochloride salt in the form of a white solid.

M.p.: 230–233° C.; MS (DCI): m/e=275 (M+H)+ e) 5-(2-(2,4-Dimethoxycinnamoylamino)ethyl)-2-(2-methoxyethoxy)benzenesulfonamide The preparation was carried out by reaction of 2.00 g (6.34 mmol) of the compound from Example 7d) with 1.32 g (6.34 mmol) of trans-2,4-dimethoxycinnamic acid according to the process described in Example 1d). After chromatographic purification on $SiO_2$ using DCM/EA (2:1) as an eluent, 2.40 g of the title compound were obtained as a white solid.

M.p.: 175–178° C.; $R_f$ (SiO2, EA)=0.13. MS (DCI): m/e=465 (M+H)+ f) 1-(5-(2-(2,4-Dimethoxycinnamoylamino)ethyl)-2-(2-methoxyethoxy)phenylsulfonyl)-3-methylthiourea The preparation was carried out according to the process described in Example 1e). In this case, there resulted from 1.30 g (2.80 mmol) of the compound from Example 7e) and 1.1 ml (1.10 mmol) of a 1-molar solution of methyl isothiocyanate in absolute DMF after chromatography on $SiO_2$ using EA/heptane (6:1) as an eluent, 857 mg of the title compound in the form of a white, amorphous foam.

$R_f$ (SiO$_2$, EA/heptane 10:1)=0.51. MS (DCI): m/e=538 (M+H)+

EXAMPLE 8

1-(5-(2-(2,4-Dimethoxycinnamoylamino)ethyl)-2-(2-methoxyethoxy)phenysulfonyl)-3-methylurea

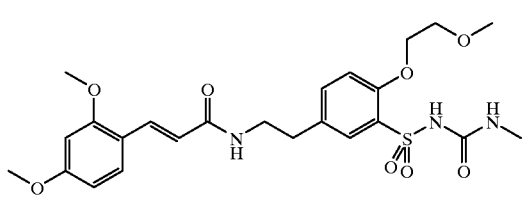

The preparation was carried out according to the process described in Example 2). From 652 mg (1.21 mmol) of the compound from Example 7f), there resulted 538 mg of the title compound in the form of an amorphous solid.

$R_f$ (SiO$_2$, EA/heptane 10:1)=0.07. MS (DCI): m/e=522 (M+H)+

EXAMPLE 9

1-(5-(2-(2,4-Dimethoxycinnamoylamino)ethyl)-2-(2-methoxyethoxy)phenylsulfonyl)-3-ethylthiourea

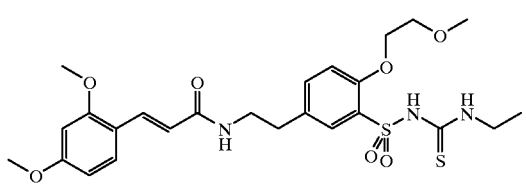

The preparation was carried out according to the process described in Example 1e), ethyl isothiocyanate being used instead of methyl isothiocyanate. There resulted from 150 mg (0.32 mmol) of the compound from Example 7e) and 32.6 µl (0.36 mmol) of ethyl isothiocyanate after chromatography on $SiO_2$ using EA/heptane (7:1) as an eluent, 139 mg of the title compound in the form of a white, amorphous foam.

M.p.: 146–148° C.; $R_f$ (SiO$_2$, EA/heptane 10:1)=0.48. MS (ESI): m/e=552 (M+H)+

EXAMPLE 10

1-(5-(2-(2,4-Dimethoxycinnamoylamino)ethyl)-2-(2-methoxyethoxy)phenylsulfonyl)-3-ethylurea

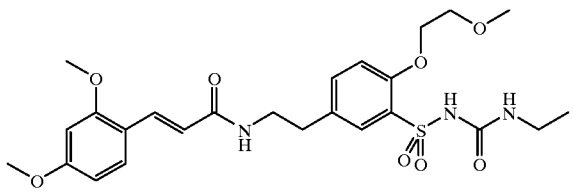

The preparation was carried out from 80 mg (0.15 mmol) of the compound from Example 9) according to the process described in Example 2). In this case, 68 mg of the title compound resulted as a pale yellow amorphous solid.

$R_f$ (SiO$_2$, EA/heptane 10:1)=0.09. MS (ESI): m/e=536 (M+H)+

EXAMPLE 11

Methyl N-(5-(2-(2,4-dimethoxycinnamoylamino)ethyl)-2-(2-methoxyethoxy)-phenylsulfonyl)carbamate

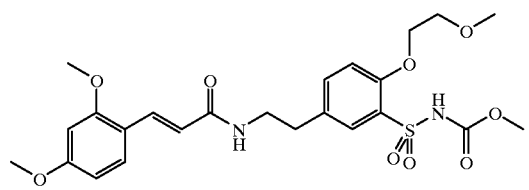

A solution of 150 mg (0.32 mmol) of the compound from Example 7e), 34.6 µl (0.32 mmol) of dimethyl pyrocarbonate, and 89 mg of potassium carbonate in 8 ml of diethylene glycol dimethyl ether was heated to reflux for 8 h. The reaction mixture was then concentrated to dryness in vacuo and the resulting residue was taken up in a mixture of DCM and 10% strength $KH_2PO_4$ solution (1:1). The organic phase was separated off, washed with $KH_2PO_4$ solution, dried using $Na_2SO_4$, and concentrated. Chromatographic purification of the residue on $SiO_2$ using EA/heptane (10:1) yielded 55 mg of the title compound as a slightly yellow-colored, amorphous solid.

$R_f$ (SiO$_2$, EA/heptane 10:1)=0.17. MS (DCI): m/e=523 (M+H)+

EXAMPLE 12

1-(5-(2-(Cinnamoylamino)ethyl)-2-methoxyphenylsulfonyl)-3-methylthiourea

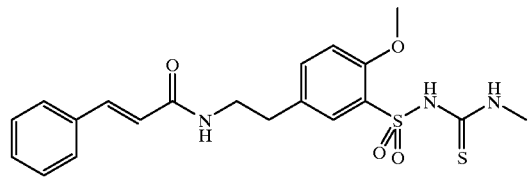

a) 5-(2-(Cinnamoylamino)ethyl)-2-methoxybenzenesulfonamide

A solution of 463 mg (3.13 mmol) of trans-cinnamic acid, 984 µl (5.73 mmol) of N-ethyldiisopropylamine, and 1.35 g (2.60 mmol) of PyBOP in 14 ml of chloroform was stirred at 50° C. for 1 h. A solution of 600 mg (2.60 mmol) of the compound from Example 1c) was added dropwise to this solution and it was then stirred at 50° C. for 2.5 h. The reaction mixture was concentrated to dryness and the residue was taken up in DCM. The solution was washed with 5% strength KHSO$_4$ and 5% strength NaHCO$_3$ solution, dried, and concentrated. The residue was purified by chromatography on SiO$_2$ using EA/heptane (5:1). Yield: 299 mg of the title compound as an amorphous solid.

R$_f$ (SiO$_2$, EA/heptane 5:1)=0.33. MS (ESI): m/e=361 (M+H)$^+$ b) 1-(5-(2-(Cinnamoylamino)ethyl)-2-methoxyphenylsulfonyl)-3-methylthiourea The preparation was carried out by reaction of 94 mg (0.26 mmol) of the compound from Example 12a) with methyl isothiocyanate according to the process described in Example 1e). Yield: 46 mg of the title compound in the form of a white, amorphous solid.

R$_f$ (SiO$_2$, EA/heptane 5:1)=0.46. MS (FAB): m/e=434 (M+H)$^+$

EXAMPLE 13

1-(5-(2-(α-Methylcinnamoylamino)ethyl)-2-methoxyphenylsulfonyl)-3-methylthiourea

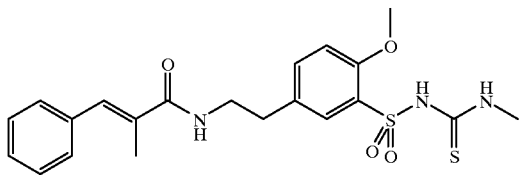

a) 5-(2-(α-Methylcinnamoylamino)ethyl)-2-methoxybenzenesulfonamide

The preparation was carried out by reaction of the compound from Example 1c) with α-methylcinnamic acid according to the process described in Example 12a).

R$_f$ (SiO$_2$, EA/heptane 4:1)=0.35. MS (DCI): m/e=375 (M+H)$^+$ b) 1-(5-(2-(α-Methylcinnamoylamino)ethyl)-2-methoxyphenylsulfonyl)-3-methylthiourea The preparation was carried out by reaction of the compound from Example 13a) with methyl isothiocyanate according to the process described in Example 1e).

R$_f$ (SiO$_2$, EA/heptane 4:1)=0.46. MS (DCI): m$^{le}$=448 (M+H)$^+$

EXAMPLE 14

1-(5-(2-(a-Phenylcinnamoylamino)ethyl)-2-methoxyphenylsulfonyl)-3-methylthiourea

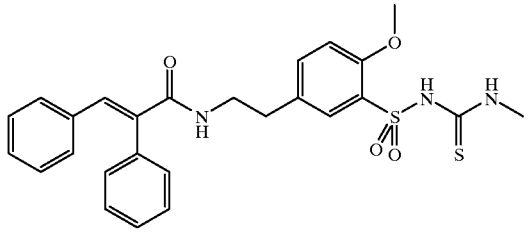

a) 5-(2-(α-Phenylcinnamoylamino)ethyl)-2-methoxybenzenesulfonamide

The preparation was carried out by reaction of the compound from Example 1c) with α-phenylcinnamic acid according to the process described in Example 12a).

R$_f$ (SiO$_2$, EA/heptane 5:1)=0.32. MS (DCI): m/e=437 (M+H)$^+$ b) 1-(5-(2-(α-Phenylcinnamoylamino)ethyl)-2-methoxyphenylsulfonyl)-3-methylthiourea The preparation was carried out by reaction of the compound from Example 14a) with methyl isothiocyanate according to the process described in Example 1e).

R$_f$ (SiO2, EA/heptane 5:1)=0.42. MS (DCI): m/e=510 (M+H)$^+$

EXAMPLE 15

1-(5-(2-(2,4-Dimethoxycinnamoylamino)ethyl)-2-phenylphenylsulfonyl)-3-methylthiourea

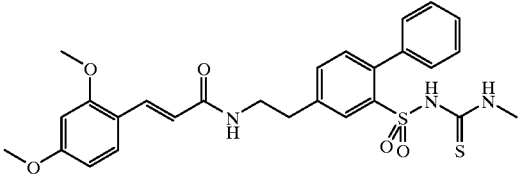

a) 2,2,2-Trifluoro-N-(2-(4-nitrophenyl)ethyl)acetamide

The preparation was carried out by reaction of 4-nitrophenylethylamine and trifluoroacetic anhydride according to the process described in Example 1a). From 29.8 g (0.15 mol) of 4-nitrophenylethylamine hydrochloride, there resulted 34.7 g of the title compound as a beige solid.

M.p.: 96–97° C.; R$_f$ (SiO$_2$, EA/heptane 1:1)=0.52. MS (ESI): m/e=263 (M+H)$^+$ b) 2,2,2-Trifluoro-N-(2-(4-aminophenyl)ethyl)acetamide A solution of 34.6 g (0.13 mol) of the compound from Example 15a) and 197 g (0.87 mol) of SnCl$_2$×2 H$_2$O in 1 l of EA was stirred at 80° C. for 3.5 h. The reaction solution was then treated with 2 l of 10% strength NaHCO$_3$ solution and the precipitate was filtered off. The organic phase was separated off, dried over Na$_2$SO$_4$, and concentrated to dryness in vacuo. 26.9 g of the title compound resulted as a pale brown solid.

M.p.: 81–85° C.; R$_f$ (SiO$_2$, EA/heptane 1:1)=0.35. MS (ESI): m/e=233 (M+H)$^+$ c) 2,2,2-Trifluoro-N-(2-(4-iodophenyl)ethyl)acetamide A solution of 8.3 g (0.12 mol) of sodium nitrite in 28 ml of water was added dropwise to a suspension of 26.8 g (0.11 mol) of the compound from Example 15b) in 125 ml of dilute hydrochloric acid cooled to 0° C. After stirring at this temperature for 15 min, a solution of 19.9 g (0.12 mol) of potassium iodide in 28 ml of water was added dropwise and the resulting reaction solution was stirred at RT for 3 h. It was extracted with DCM, and the organic phase was separated off, washed with 10% strength NaHSO$_3$ solution and water, and dried over Na$_2$SO$_4$. After concentration and chromatographic purification of the residue on SiO$_2$ using DCM/EA (80:1) as an eluent, 17.1 g of the title compound were obtained in the form of a pale yellow solid.

M.p.: 136–138° C.; R$_f$ (SiO$_2$, EA/heptane 1:1) 0.67. MS (DCI): m/e=344 (M+H)$^+$ d) 2-Iodo-5-(2-(2,2,2-trifluoroacetamido)ethyl)benzenesulfonamide 10 g (29.1 mmol) of the compound from Example 15c) were added in portions to 95 ml of chlorosulfonic acid cooled to 0° C. After stirring at RT for 3.5 h, the reaction solution was added dropwise to 400 ml of ice and the precipitate deposited was filtered off with suction. This precipitate was dissolved in 200 ml of acetone and 56 ml of concentrated ammonia solution were added dropwise to the solution with ice cooling. After stirring at RT for 45 min, the precipitate deposited was filtered off with suction and the acetone was stripped off on a rotary evaporator. The solution that remained was extracted with EA, and the EA phase was separated off, washed with saturated NaCl solution, and dried over $Na_2SO_4$. After concentration and chromatographic purification of the residue on $SiO_2$ using EA/heptane (1:2) as an eluent, 4.5 g of the title compound were obtained.

M.p.: softening from 100° C.; $R_f$ ($SiO_2$, EA/heptane 1:1)=0.32. MS (ESI): m/e=423 (M+H)$^+$ e) 5-(2-Aminoethyl)-2-iodobenzenesulfonamide A solution of 4.0 g (9.47 mmol) of the compound from Example 15d) in 25 ml of 2 N hydrochloric acid was stirred at reflux for 4.5 h. The pH of the solution was then adjusted to 10 by addition of 2 N sodium hydroxide solution and it was extracted several times with EA. The organic phase was dried over $Na_2SO_4$ and concentrated. The residue which remained was combined with the precipitate deposited from the aqueous phase and filtered off with suction. After drying under high vacuum, 2.65 g of the title compound resulted.

M.p.: 215° C.; $R_f$ (SiO2, EA/heptane 1:1)=0.10. MS (ESI): m/e=327 (M+H)$^+$ f) 5-(2-(2,4-Dimethoxycinnamoylamino)ethyl)-2-iodobenzenesulfonamide A solution of 693 mg (3.33 mmol) of trans-2,4-dimethoxycinnamic acid and 583 mg (3.60 mmol) of carbonylbisimidazole in 25 ml of THF was stirred at RT for 2 h. 1.2 g (3.73 mmol) of the compound from Example 15e) were then added to this solution and the solution was stirred at RT for 24 h. The reaction solution was poured onto 70 ml of 1 N hydrochloric acid, extracted with EA, and the organic extracts were dried over $Na_2SO_4$ and concentrated. The residue was stirred with EA, and the precipitate which remained was filtered off with suction and purified by chromatography on SiO2 using EA/heptane (2:1) as an eluent. 1.2 g of the title compound resulted in the form of a pale yellow solid.

M.p: 180° C.; $R_f$ ($SiO_2$, EA/heptane 2:1)=0.26. MS (FAB): m/e=517 (M+H)$^+$ g) 5-(2-(2,4-Dimethoxycinnamoylamino)ethyl)-N-dimethylaminomethylene-2-iodobenzenesulfonamide A solution of 1.1 g (2.15 mmol) of the compound from Example 16f) and 346 µl (2.58 mmol) of N,N-dimethylformamide dimethyl acetal in 8 ml of absolute DMF was stirred at RT for 1 h. It was concentrated to dryness in vacuo, the residue was taken up in DCM, and the solution was washed with water and NaCl solution and concentrated. Chromatographic purification of the residue on $SiO_2$ using DCM/methanol (20:1) as an eluent yielded 998 mg of the title compound in the form of an amorphous, yellow foam.

$R_f$ ($SiO_2$, EA/heptane 7:3)=0.10. MS (ESI): m/e=572 (M+H)$^+$ h) 5-(2-(2,4-Dimethoxycinnamoylamino)ethyl)-N-dimethylaminomethylene-2-phenylbenzenesulfonamide A solution of 53 mg (0.44 mmol) of phenylboronic acid in 2.5 ml of ethanol was added dropwise in an argon atmosphere to a solution of 250 mg (0.44 mmol) of the compound from Example 15g) and 16 mg (0.01 mmol) of tetrakis(triphenylphosphine)palladium in 2.5 ml of toluene. After stirring at RT for 15 min, 510 µl of a 2-molar cesium carbonate solution were added and the resulting reaction mixture was stirred at 80° C. for 6 h. It was concentrated in vacuo, the residue was taken up in DCM, and the solution was washed several times with water, dried over $Na_2SO_4$, and concentrated. Chromatographic purification of the residue on $SiO_2$ using EA as an eluent yielded 207 mg of the title compound in the form of an amorphous, beige solid.

$R_f$ ($SiO_2$, EA)=0.25. MS (FAB): m/e=522 (M+H)$^+$ i) 5-(2-(2,4-Dimethoxycinnamoylamino)ethyl)-2-phenylbenzenesulfonamide A solution of 202 mg (0.39 mmol) of the compound from Example 15h) and 1 ml of conc. hydrochloric acid in 5 ml of methanol was heated at reflux for 4 h. The pH of the reaction solution was then adjusted to 5 by addition of 2 N sodium hydroxide solution and it was then extracted several times with EA. The combined EA extracts were dried over $Na_2SO_4$ and concentrated. Chromatographic purification of the residue on $SiO_2$ using EA/toluene (5:1) as an eluent yielded 78 mg of the title compound in the form of a beige solid.

M.p: 85° C. (softening). $R_f$ ($SiO_2$, EA/toluene 5:1)=0.48. MS (ESI): m/e=467 (M+H)$^+$ j) 1-(5-(2-(2,4-Dimethoxycinnamoylamino)ethyl)-2-phenylphenylsulfonyl)-3-methylthiourea The preparation was carried out by reaction of 64 mg (0.14 mmol) of the compound from Example 15i) with methyl isothiocyanate according to the process described in Example 1e). In this case, there resulted 68 mg of the title compound in the form of a pale yellow, amorphous solid.

$R_f$ ($SiO_2$, EA/heptane 2:1)=0.29. MS (ESI): m/e=540 (M+H)$^+$

EXAMPLE 16

1-(5-(2-(2,4-Dimethoxycinnamoylamino)ethyl)-2-(2-furyl)phenylsulfonyl)-3-methylthiourea

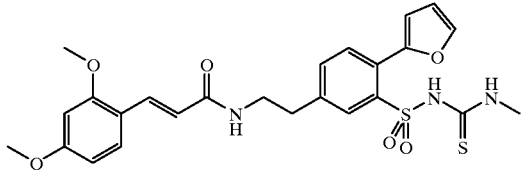

a) 5-(2-(2,4-Dimethoxycinnamoylamino)ethyl)-N-dimethylaminomethylene-2-(2-furyl)benzenesulfonamide 2.7 mg (0.004 mmol) of bis(triphenylphosphine)palladium(II) chloride and 305 µl (0.97 mmol) of 2-(tributylstannyl)furan were added to a solution of 400 mg (0.70 mmol) of the compound from Example 15g) in 5 ml of THF in an argon atmosphere. The resulting reaction solution was heated at reflux for 18 h. It was then diluted with EA, and the solution was washed with water, dried over $Na_2SO_4$, and concentrated. Chromatographic purification of the residue on $SiO_2$ using EA as an eluent afforded 287 mg of the title compound in the form of an amorphous, white foam.

$R_f$ (SiO2, EA)=0.35. MS (ESI): m/e=512 (M+H)$^+$ b) 5-(2-(2,4-Dimethoxycinnamoylamino)ethyl)-2-(2-furyl)benzenesulfonamide The preparation was carried out by treatment of 281 mg (0.55 mmol) of the compound from Example 16a) with hydrochloric acid according to the process described in Example 15i). After chromatographic purification on $SiO_2$ using EA as an eluent, 82 mg of the title compound were obtained in the form of a yellow-colored, amorphous solid.

$R_f$ ($SiO_2$, EA)=0.72. MS (ESI): m/e=457 (M+H)$^+$ c) 1-(5-(2-(2,4-Dimethoxycinnamoylamino)ethyl)-2-(2-furyl)phenylsulfonyl)-3-methylthiourea The preparation was carried out by reaction of 52 mg (0.14 mmol) of the compound from Example 16b) with methyl isothiocyanate according to the process described in Example 1e). Yield: 28 mg of the title compound in the form of an amorphous solid.

$R_f$ (SiO$_2$, EA/heptane 2:1)=0.18. MS (ESI): m/e=530 (M+H)$^+$

EXAMPLE 17

1-(5-(2-(Cinnamoylamino)ethyl)-2-(2-methoxyethoxy)phenylsulfonyl)-3-methylthiourea

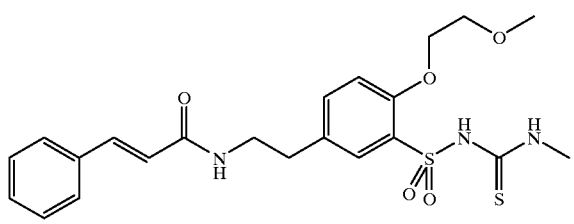

a) 5-(2-(Cinnamoylamino)ethyl)-2-(2-methoxyethoxy)benzenesulfonamide

The title compound was prepared by reaction of the compound from Example 7d) with trans-cinnamic acid according to the process mentioned in Example 5a). From 1.75 g (5.62 mmol) of the compound from Example 7d) and 1.0 g (6.75 mmol) of trans-cinnamic acid, there resulted, after crystallization by trituration with a little EA, 910 mg of the title compound as a white solid.

M.p.: 133° C.; $R_f$ (SiO$_2$, EA/heptane 4:1)=0.24. MS (ESI): m/e=405 (M+H)$^+$ b) 1-(5-(2-(Cinnamoylamino)ethyl)-2-(2-methoxyethoxy)phenylsulfonyl)-3-methylthiourea The title compound was prepared by reaction of the compound from Example 17a) with methyl isothiocyanate according to the process mentioned in Example 1e). From 600 mg (1.48 mmol) of the compound from Example 17a), there resulted after chromatography on SiO$_2$ using EA as an eluent 401 mg of the title compound as a white solid.

M.p.: 150° C. (softening). $R_f$(SiO$_2$, EA)=0.75. MS (ESI): m/e=478 (M+H)$^+$

EXAMPLE 18

1-(5-(2-(Cinnamoylamino)ethyl)-2-(2-methoxyethoxy)phenysulfonyl)-3-methylthiourea sodium salt

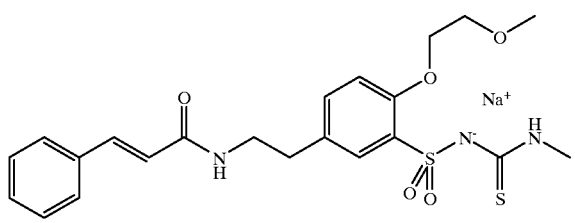

24.1 mg (1.05 mmol) of sodium were dissolved in 13.5 ml of absolute methanol. 500 mg (1.05 mmol) of the compound from Example 17b) were then added and the resulting solution was stirred at RT for 1 h. After addition of 90 ml of isopropanol and storage in a refrigerator for 2 days, the precipitate which crystallized out was filtered off with suction and washed with a little isopropanol. After drying under high vacuum, 441 mg of the title compound were obtained in the form of a white solid.

M.p.: 245° C.; MS (ESI): m/e=500 (M+H)$^+$

EXAMPLE 19

1-(5-(2-(Cinnamoylamino)ethyl)-2-(2-methoxyethoxy)phenylsulfonyl)-3-methylurea

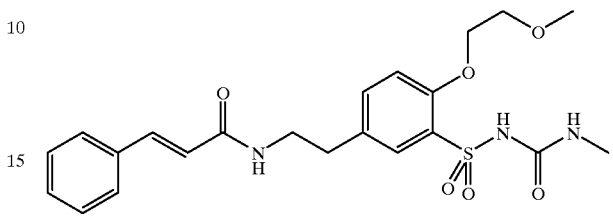

The title compound was prepared by treatment of the compound from Example 17b) with hydrogen peroxide according to the process mentioned in Example 2. From 48 mg (0.1 mmol) of the compound from Example 17b), there resulted 25 mg of the title compound as a white solid.

M.p.: 65° C. (softening). $R_f$ (SiO$_2$, EA)=0.10. MS (ESI): m/e=462 (M+H)$^+$

EXAMPLE 20

1-(2-Benzyloxy-5-(2-(2,4-dimethoxycinnamoylamino)ethyl)phenylsulfonyl)-3-methylthiourea

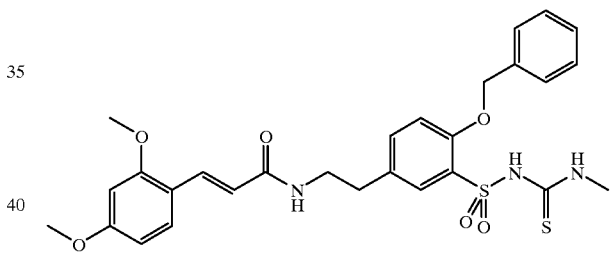

a) 2-Benzyloxy-N-dimethylaminomethylene-5-(2-(2,2,2-trifluoroacetamido)ethyl)-benzenesulfonamide A mixture of 2.76 g (7.51 mmol) of the compound from Example 7b), 3.13 ml (26.3 mmol) of benzyl bromide, and 2.62 g (18.8 mmol) of potassium carbonate in 20 ml of absolute DMF was stirred at 70° C. for 6 h, and was then diluted with DCM and treated with water. The organic phase was separated off, washed with saturated NaCl solution, and dried over Na$_2$SO$_4$. After concentration and chromatographic purification of the residue on SiO$_2$ using DCM/EA (4:1) as an eluent, 1.9 g of the title compound resulted as a white solid.

M.p.: 103° C. (softening). $R_f$ (SiO$_2$, DCM/EA 4:1)=0.26. MS (ESI): m/e=458 (M+H)$^+$ b) 5-(2-Aminoethyl)-2-benzyloxybenzenesulfonamide The title compound was prepared by treatment of the compound from Example 20a) with 2 N HCl according to the process mentioned in Example 7d). From 1.88 g (4.13 mmol) of the compound from Example 20a), there resulted 1.2 g of the title compound as a white solid.

M.p.: 210° C.; $R_f$ (SiO$_2$, EA)=0.02. MS (ESI): m/e=307 (M+H)$^+$ c) 2-Benzyloxy-5-(2-(2,4-dimethoxycinnamoylamino)ethyl)benzenesulfonamide The title compound was prepared by reaction of the compound from Example 20b) with trans-2,4-dimethoxycinnamic acid according to the process mentioned in Example 5a). In this case, there resulted from 1.2 g (4.1 mmol) of the compound from Example 20b) 503 mg of the title compound as a white solid.

M.p.: 133° C.; $R_f$ (SiO$_2$, EA/heptane 2:1)=0.43. MS (ESI): m/e=497 (M+H)$^+$ d) 1-(2-Benzyloxy-5-(2-(2,4-dimethoxycinnamoyl)ethyl) phenylsulfonyl)-3-methylthiourea The title compound was prepared by reaction of the compound from Example 20c) with methyl isothiocyanate according to the process mentioned in Example 1e). From 181 mg (0.36 mmol) of the compound from Example 20c), there resulted 204 mg of the title compound as a beige, amorphous solid.

$R_f$ (SiO$_2$, EA/heptane 2:1)=0.23. MS (ESI): m/e=570 (M+H)$^+$

EXAMPLE 21

1-(5-(2-(5–Chloro-2-methoxycinnamoylamino) ethyl)-2-methoxyphenylsulfonyl)-3-methylthiourea

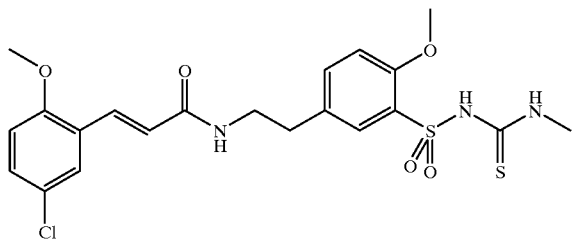

a) Ethyl 5-chloro-2-methoxycinnamate

A solution of 10.6 g (48.2 mmol) of 2-bromo-4-chloroanisole in 30 ml of triethylamine was treated with 1 0.1 ml (81.2 mmol) of ethyl acrylate, 1.23 g of tri-o-tolylphosphine, and 0.45 g of palladium(II) acetate in an argon atmosphere. The reaction mixture was stirred at 100° C. for 2 days, then diluted with EA and filtered through Celite. The filtrate was washed with 1 N HCl and saturated NaCl solution, dried over Na$_2$SO$_4$, and concentrated. After chromatographic purification over SiO$_2$ using EA/heptane (1:8) as an eluent, 0.85 g of the title compound resulted as a pale yellow oil.

$R_f$ (SiO$_2$, EA/heptane 1:4)=0.34. MS (ESI): m/e=241 (M+H)$^+$ b) 5-Chloro-2-methoxycinnamic acid A solution of 0.84 g (3.46 mmol) of the compound from Example 21a) in 2 ml of ethanol and 1 ml of water was treated with 0.67 g (12 mmol) of potassium hydroxide and stirred at RT for 45 min. The ethanol was then stripped off in vacuo in a rotary evaporator, the residue was diluted with 10 ml of water, and the pH of the solution was adjusted to 1 by addition of 2 N HCl. The precipitate deposited was filtered off with suction, washed with water, and dried at 40° C. under high vacuum. 545 mg of the title compound were obtained as a white solid.

M.p: 188–190° C.; $R_f$ (SiO$_2$, EA/heptane 1:2)=0.14. MS (ESI): m$^{ie}$=213 (M+H)$^+$ c) 5-(2-(5–Chloro-2-methoxycinnamoylamino)ethyl)-2-methoxybenzenesulfonamide The title compound was prepared by reaction of the compound from Example 21b) with the compound from Example 1c) according to the process mentioned in Example 5a). From 350 mg (1.64 mmol) of the compound from Example 21b) and 315 mg (1.37 mmol) of the compound from Example 1c), there resulted 470 mg of the title compound as a white solid.

M.p.: 196–198° C.; $R_f$ (SiO$_2$, EA/heptane 4:1)=0.13. MS (ESI): m/e=425 (M+H)$^+$ d) 1-(5-(2-(5–Chloro-2-methoxycinnamoylamino)ethyl)-2-methoxyphenylsulfonyl)-3-methylthiourea The title compound was prepared by reaction of the compound from Example 21c) with methyl isothiocyanate according to the process mentioned in Example 1e). From 100 mg (0.24 mmol) of the compound from Example 21c), there resulted 93 mg of the title compound as a white solid.

M.p: 188–190° C.; $R_f$ (SiO$_2$, EA/heptane 4:1)=0.33. MS (ESI): m/e=499 (M+H)$^+$ a) Ethyl 5-chloro-2-methoxycinnamate

EXAMPLE 22

1-(5-(2-(2,4-Dimethoxycinnamoylamino)ethyl)-2-phenoxyphenylsulfonyl)-3-methylthiourea

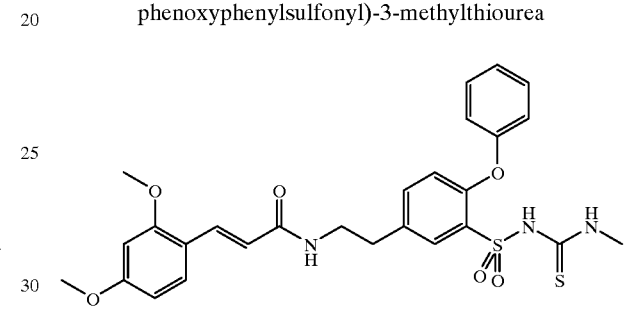

a) N-Dimethylaminomethylene-2-phenoxy-5-(2-(2,2,2-trifluoroacetamido)ethyl)-benzenesulfonamide A mixture of 500 mg (1.36 mmol) of the compound from Example 7b), 247 mg (1.36 mmol) of copper(II) acetate, 498 mg (4.08 mmol) of phenylboronic acid, and 943 μl (6.80 mmol) of triethylamine in 15 ml of DCM was stirred at RT for 24 h under an argon atmosphere in the presence of ground and dried molecular sieve. The reaction mixture was filtered, and the filtrate was washed with 10% strength KHSO$_4$ solution and 10% strength NaHCO$_3$ solution, dried over Na$_2$SO$_4$, and then concentrated. After chromatographic purification on SiO$_2$ using EA/heptane (3:1), there resulted 197 mg of the title compound as a white, amorphous foam.

$R_f$ (SiO$_2$, EA)=0.72. MS (ESI): m/e=444 (M+H)$^+$ b) 5-(2-Aminoethyl)-2-phenoxybenzenesulfonamide The title compound was prepared by treatment of the compound from Example 22a) with 2 N HCl according to the process mentioned in Example 7d). From 149 mg (0.34 mmol) of the compound from Example 22a), there resulted 98 mg of the title compound as a white, amorphous solid.

$R_f$ (SiO$_2$, EA)=0.02. MS (ESI): m/e=293 (M+H)$^+$ c) 5-(2-(2,4-Dimethoxycinnamoylamino)ethyl)-2-phenoxybenzenesulfonamide The title compound was prepared by reaction of the compound from Example 22b) with trans-2,4-dimethoxycinnamic acid according to the process mentioned in Example 5a). In this case, there resulted from 96 mg (0.33 mmol) of the compound from Example 22b) 90 mg of the title compound as a pale yellow, amorphous solid.

$R_f$ (SiO$_2$, EA/heptane 2:1)=0.27. MS (ESI): m/e=483 (M+H)$^+$ d) 1-(5-(2-(2,4-Dimethoxycinnamoylamino)ethyl)-2-phenoxyphenylsulfonyl)-3-methylthiourea The title compound was prepared by reaction of the compound from Example 22c) with methyl isothiocyanate according to the process mentioned in Example 1e). From 85 mg (0.18 mmol) of the compound from Example 22c), there resulted 77 mg of the title compound as a beige, amorphous solid.

$R_f$ (SiO$_2$, EA/heptane 2:1)=0.23. MS (ESI): m/e=556 (M+H)$^+$

EXAMPLE 23

1-(2-Allyloxy-5-(2-(2,4-dimethoxycinnamoylamino) ethyl)phenylsulfonyl)-3-methylthiourea

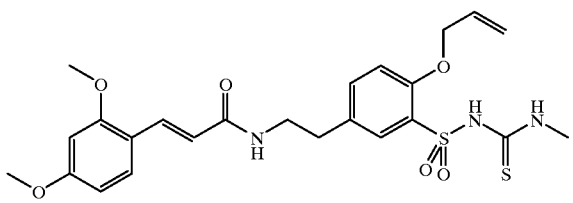

a) 2-Allyloxy-N-dimethylaminomethylene-5-(2-(2,2,2-trifluoroacetamido)ethyl)-benzenesulfonamide A solution of 2.0 g (0.54 mmol) of the compound from Example 7b) and 1.65 ml (19.0 mmol) of allyl bromide in 15 ml of absolute DMF was treated with 1.9 g (13.6 mmol) of potassium carbonate and stirred at 70° C. for 6 h. The reaction mixture was diluted with DCM and water was added. The separated organic phase was washed with saturated NaCl solution, dried over Na$_2$SO$_4$, and concentrated. Chromatographic purification of the residue on SiO$_2$ using DCM/EA (4:1) as an eluent afforded 1.2 g of the title compound as a white solid.

M.p.: 92–93° C.; $R_f$(SiO$_2$, EA)=0.52. MS (ESI): m/e=408 (M+H)$^+$ b) 2-Allyloxy-5-(2-aminoethyl)benzenesulfonamide The title compound was prepared by treatment of the compound from Example 23a) with 2 N HCl according to the process mentioned in Example 7d). From 1.2 g (2.95 mmol) of the compound from Example 23a), there resulted 550 mg of the title compound as a white solid.

M.p.: 195° C.; $R_f$ (siO$_2$, EA)=0.02. MS (ESI): m/e=257 (M+H)$^+$ c) 2-Allyloxy-5-(2-(2,4-dimethoxycinnamoylamino)ethyl) benzenesulfonamide The title compound was prepared by reaction of the compound from Example 23b) with 2,4-dimethoxycinnamic acid according to the process mentioned in Example 5a). From 1.55 g (6.05 mmol) of the compound from Example 23b) and 1.26 g (6.05 mmol) of 2,4-dimethoxycinnamic acid, there resulted 430 mg of the title compound as a pale yellow solid.

M.p.: 166–168° C.; $R_f$(SiO$_2$, EA/heptane 2:1)=0.26. MS (ESI): m/e=447 (M+H)$^+$ d) 1-(2-Allyloxy-5-(2-(2,4-dimethoxycinnamoylamino) ethyl)phenylsulfonyl)-3-methylthiourea The title compound was prepared by reaction of the compound from Example 23c) with methyl isothiocyanate according to the process mentioned in Example 1e). From 180 mg (0.40 mmol) of the compound from Example 23c), there resulted 110 mg of the title compound as a pale yellow solid.

M.p.: 171–175° C.; $R_f$(SiO$_2$, EA/heptane 4:1)=0.18. MS (ESI): m/e=520 (M+H)$^+$

EXAMPLE 24

1-(5-(2-(2,4-Dichlorocinnamoylamino)ethyl)-2-(2-methoxyethoxy)phenyl(sulfonyl)-3-methylthiourea

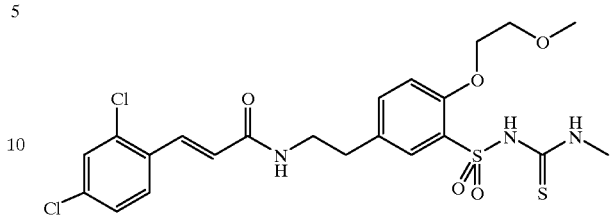

a) 5-(2-(2,4-Dichlorocinnamoylamino)ethyl)-2-(2-methoxyethoxy)benzenesulfonamide The title compound was prepared by reaction of the compound from Example 7d) with 2,4-dichlorocinnamic acid according to the process mentioned in Example 5a). From 1.6 g (5.15 mmol) of the compound from Example 7d) and 1.08 g (6.18 mmol) of 2,4-dichlorocinnamic acid, there resulted 1.56 g of the title compound as a white solid.

$R_f$ (SiO$_2$, EA/heptane 4:1)=0.14. MS (ESI): m/e=474 (M+H)$^+$ b) 1-(5-(2-(2,4-Dichlorocinnamoylamino)ethyl)-2-(2-methoxyethoxy)phenylsulfonyl)-3-methylthiourea The title compound was prepared by reaction of the compound from Example 24a) with methyl isothiocyanate according to the process mentioned in Example 1e). From 150 mg (0.32 mmol) of the compound from Example 24a), there resulted 143 mg of the title compound as a white solid.

M.p.: 76–78° C.; $R_f$ (SiO$_2$, EA/heptane 4:1)=0.18. MS (ESI): m/e=547 (M+H)$^+$

EXAMPLE 25

1-(5-(2-(5-tert-Butyl-2-methoxycinnamoylamino) ethyl)-2-(2-methoxyethoxy)phenyl-sulfonyl)-3-methylthiourea

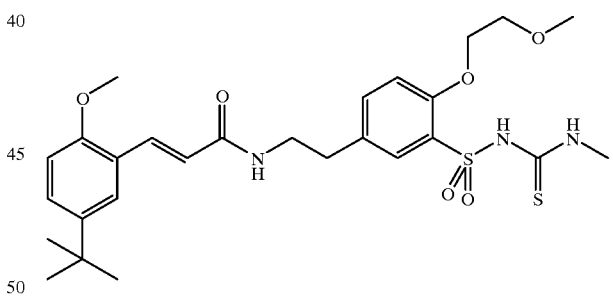

a) 4-tert-Butyl-2-iodoanisole

A solution of 8 g (0.11 mol) of sodium nitrite in 25 ml of water was added dropwise to a solution of 20 g (0.11 mol) of 5-tert-butyl-2-methoxyaniline in 120 ml of water/conc. HCL (1:1) cooled to 5° C. After stirring at 5° C. for 15 min, a solution of 19.1 g (0.11 mol) of potassium iodide in 25 ml of water was added dropwise and the solution obtained was stirred at RT for 4 h. It was extracted several times with DCM, and the separated organic phase was washed with 10% strength NaHSO$_3$ solution and water, dried over Na$_2$SO$_4$, and concentrated. Chromatographic purification of the residue which remained on SiO$_2$ using EA/heptane (1:40) yielded 27 g of the title compound in the form of a pale red oil.

$R_f$ (SiO$_2$, EA/heptane 1:1)=0.86. MS (ESI): m/e=291 (M+H)$^+$ b) Ethyl 5-tert-butyl-2-methoxycinnamate A solution of 25 g (86.4 mmol) of the compound from Example 25a), 18.1 ml (145.6 mmol) of ethyl acrylate, 2.2 g (7.23 mmol) of tri-o-tolylphosphine, and 814 mg (3.62 mmol) of palladium(II) chloride was stirred at 60° C. for 2 h under an argon atmosphere. The reaction mixture was then diluted with 150 ml of EA, the precipitate was filtered off, and the filtrate was washed with 1 N HCl and saturated NaCl solution. After drying over Na$_2$SO$_4$, concentration, and chromatographic purification of the residue that remained on SiO$_2$ using EA/heptane (1:20) as an eluent, 19.7 g of the title compound resulted as a pale yellow oil.

R$_f$ (SiO$_2$, EA/heptane 1:10)=0.30. MS (ESI): m/e=263 (M+H)$^+$ c) 5-tert-Butyl-2-methoxycinnamic acid The title compound was prepared by treatment of the compound from Example 25b) with KOH according to the process mentioned in Example 21b). In this case, there resulted from 19.7 g (75.1 mmol) of the compound from Example 25b) 17.5 g of the title compound as a pale grey solid.

M.p.: 165–167° C.; R$_f$ (SiO$_2$, EA/heptane 1:10)=0.04. MS (ESI): m/e=235 (M+H)$^+$ d) 5-(2-(5-tert-Butyl-2-methoxycinnamoylamino)ethyl)-2-(2-methoxyethoxy)benzenesulfonamide The title compound was prepared by reaction of the compound from Example 7d) with the compound from Example 25c) according to the process mentioned in Example 5a). From 1.1 g (3.56 mmol) of the compound from Example 7d) and 1.0 g (4.27 mmol) of the compound from Example 25c), there resulted 866 mg of the title compound as a white solid.

M.p.: 154° C.; R$_f$ (SiO$_2$, EA/heptane 2:1)=0.13. MS (ESI): m/e=491 (M+H)$^+$ e) 1-($^5$-(2-(5-tert-Butyl-2-methoxycinnamoylamino)ethyl)-2-(2-methoxyethoxy)phenylsulfonyl)-3-methylthiourea The title compound was prepared by reaction of the compound from Example 25d) with methyl isothiocyanate according to the process mentioned in Example 1e). From 286 mg (0.58 mmol) of the compound from Example 25d), there resulted 327 mg of the title compound as a white solid.

M.p: 73° C. (softening). R$_f$ (SiO$_2$, EA)=0.64. MS (ESI): m/e=564 (M+H)$^+$

EXAMPLE 26

1-(5-(2-(2,4-Dimethylcinnamoylamino)ethyl)-2-(2-methoxyethoxy)phenylsufonyl)-3-methylthiourea

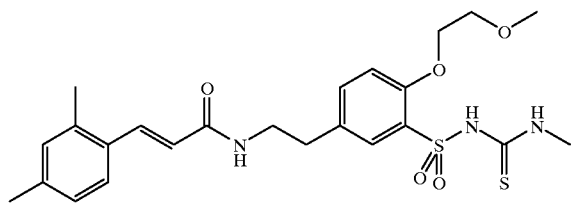

a) 5-(2-(2,4-Dimethylcinnamoylamino)ethyl)-2-(2-methoxyethoxy)benzenesulfonamide The title compound was prepared by reaction of the compound from Example 7d) with trans-2,4-dimethylcinnamic acid according to the process mentioned in Example 5a). From 1.6 g (5.15 mmol) of the compound from Example 7d) and 1.0 g (6.15 mmol) of trans-2,4-dimethylcinnamic acid, there resulted after chromatography on SiO$_2$ using EA/heptane (4:1) as an eluent 1.05 g of the title compound as a white solid.

R$_f$ (SiO$_2$, EA/heptane 4:1)=0.09. MS (ESI): m/e=432 (M+H)$^+$ b) 1-(5-(2-(2,4-Dimethylcinnamoylamino)ethyl)-2-(2-methoxyethoxy)phenylsulfonyl)-3-methylthiourea The title compound was prepared by reaction of the compound from Example 26a) with methyl isothiocyanate according to the process mentioned in Example 1e). From 150 mg (0.35 mmol) of the compound from Example 26a), there resulted 134 mg of the title compound as a beige, amorphous solid.

M.p.: 116° C.; R$_f$ (SiO$_2$, EA/heptane 2:1)=0.16. MS (ESI): m/e=506 (M+H)$^+$ Pharmacological investigations Action potential duration in the papillary muscle of the guinea pig ATP deficiency states, such as are observed during ischemia in the cardiac muscle cell, lead to a shortening of the action potential duration. They are regarded as one of the causes of so-called reentry arrhythmias, which can cause sudden cardiac death. The opening of ATP-sensitive potassium channels by the lowering of the ATP level is regarded as causing this (ATP=adenosine triphosphate). For the measurement of the action potential in the papillary muscle of the guinea pig a standard microelectrode technique was employed.

Guinea pigs of both sexes were killed by a blow to the head, the hearts were removed, and the papillary muscles were separated out and suspended in an organ bath. The organ bath was irrigated with Ringer's solution (136 mmol/l of NaCl, 3.3 mmol/l of KCl, 2.5 mmol/l of CaCl$_2$, 1.2 mmol/l of KH$_2$PO$_4$, 1.1 mmol/l of MgSO$_4$, 5.0 mmol/l of glucose, and 10.0 mmol/l of N-(2-hydroxyethyl)piperazine-N'-(2-ethanesulfonic acid) (HEPES), pH adjusted to 7.4 with NaOH) and aerated with 100% oxygen at a temperature of 37° C. The muscle was stimulated by means of an electrode using square-wave impulses of 1 V and 1 ms duration and a frequency of 1 Hz. The action potential was derived and recorded by means of a glass microelectrode inserted intracellularly, which was filled with 3 mol/l of KCl solution. The substance to be tested was added to the Ringer's solution in a concentration of 2 µmol/l. The action potential was amplified using an amplifier from Hugo Sachs (March-Hugstetten, Germany) and stored and analyzed by means of a computer. The duration of the action potential was determined at a degree of repolarization of 90% (APD$_{90}$). The action potential shortening was produced by addition of a solution of the potassium channel opener Rilmakalim (HOE 234) (W. Linz et al., *Arzneimittelforschung/Drug Research*, 42 (II) (1992) 1180–1185) (rilmakalim concentration 1 µg/ml). 30 minutes after the administration of rilmakalim, the action potential duration was recorded. The test substance was then added and the action potential duration, which was prolonged again, was recorded after a further 60 minutes. The test substances were added to the bath solution as stock solutions in propanediol.

The following APD$_{90}$ values (in milliseconds) were recorded.

| Test substance | Starting value | + HOE 234, 30 min | + HOE 234, 30 min, then + test substance, 60 min |
|---|---|---|---|
| Example 1 | 185 | 24 | 177 |
| Example 7 | 192 | 34 | 175 |
| Example 8 | 193 | 34 | 92 |

The measured values confirm the normalizing action of the substances according to the invention on a shortened action potential duration.

Chloroform-induced ventricular fibrillation in the mouse (action in the case of vagal dysfunction)

A hypofunction of the vagal nervous system leads to a hyperfunction of the sympathetic nervous system. Damages to health which result from an imbalance of the autonomic nervous system if the dysfunction relates to the heart, include weakening of the myocardial contractile force and fatal cardiac arrhythmias such as ventricular fibrillation. The action of the test substances was investigated in the model of chloroform-induced ventricular fibrillation in the mouse (see J. W. Lawson, "Antiarrhythmic activity of some isoquinoline derivatives determined by a rapid screening procedure in the mouse," *J. Pharmacol. Exp. Ther.* 160 (1968) 22).

The test substance was dissolved in a mixture of dimethyl sulfoxide (DMSO) and 10 percent sodium hydrogen carbonate solution and administered intraperitoneally (i.p.). The dose was 3 mg/kg. 30 minutes later, the mouse was anesthetized with chloroform in a beaker. As soon as respiratory arrest had occurred under deep anesthesia (toxic anesthesia stage), the thorax of the animal was opened with a pair of scissors and the heartbeat was visually inspected. It can be detected at a glance here whether the heart is beating, fibrillating, or has stopped. The respiratory arrest induced by chloroform leads, via absolute anoxia (oxygen deficiency) in combination with a direct stimulating action of chloroform on the sympathetic nervous system, to a strong stimulation of the sympathetic nervous system which in turn leads, in combination with the energy deficiency produced in the heart by oxygen deficiency, to the fatal arrhythmia, ventricular fibrillation. This toxic chloroform anesthesia led to ventricular fibrillation in 100% of the untreated mice (control). The percentage proportion of the mice having ventricular fibrillation in the individual test groups (with n animals) is indicated as the fibrillation ratio.

The following fibrillation ratios were determined.

| Test substance | Fibrillation ratio (in %) |
|---|---|
| Untreated control (n = 300) | 100% |
| Example 1 (n = 10) | 60% |
| Example 5 (n = 10) | 70% |
| Example 8 (n = 10) | 60% |
| Example 9 (n = 10) | 63% |
| Example 12 (n = 10) | 63% |

The reduction in the percentage proportion of mice with ventricular fibrillation in comparison with the control (with a 100% fibrillation ratio) confirms that compounds of formula I significantly prevent the occurrence of ventricular fibrillation.

The observed effect of atropine, the classical blocker of muscarinergic (vagal) receptors of the autonomic nervous system which blocks the action of the vagal transmitter acetylcholine at the level of the receptor, allows a conclusion to be made about the mechanism of action. The experiment is carried out here as described above. The compound of Example 8 was administered to the animals of the first experimental group (n=number of animals=20) in an amount of 10 mg/kg i.p. 30 min after the administration, the animals were anesthetized with chloroform and the fibrillation ratio was determined. Atropine was administered to the animals of the second experimental group (n=10) in an amount of 1 mg/kg i.v. 15 min after the administration, the animals were anesthetized with chloroform and the fibrillation ratio was determined. First the compound of Example 8 in an amount of 10 mg/kg i.p. and then, after 15 min, atropine in an amount of 1 mg/kg i.v. were administered to the animals of the third group (n=10). After a further 15 min, the animals were anesthetized with chloroform and the fibrillation ratio was determined.

| | Example 8 (10 mg/kg, i.p.) n = 20 | Atropine (1 mg/kg, i.v.) n = 10 | Combination Example 8 + atropine n = 10 |
|---|---|---|---|
| Number of animals with fibrillation | 9 | 10 | 9 |
| Number of animals with regular heart action | 11 | 0 | 1 |
| Fibrillation ratio | 45% [1), 2)] | 100% | 90% |

[1)] p < 0.0001 in the chi-squared test or Fisher's exact test; decrease in the ventricular fibrillation compared with controls (atropine)
[2)] p = 0.024 in the chi-squared test or Fisher's exact test; decrease in the ventricular fibrillation compared with combination The results show that atropine decreases or prevents the protective action of compounds of formula I. This abolition of the protective action of compounds of formula I by atropine clearly points to a vagal mechanism of action.

The lacking or only very low hypoglycemic action of compounds of formula I can be determined, for example, by determination of the membrane potential on isolated β cells of the pancreas, for example, according to the method described in U.S. Pat. No. 5,698,596 or EP-A-612 724 whose relevant contents are part of the present disclosure and which are incorporated herein by reference, or it can be shown in suitable mammalian cells, for example CHO cells which are transfected with human SUR1/Kir6.2 proteins as molecular constituents of pancreatic ATP-sensitive potassium channels.

The present invention may be embodied in other specific forms without departing from its spirit or essential characteristics. The described embodiments are to be considered in all respects as illustrative only and not restrictive. The scope of the invention is, therefore, indicated by the appended claims rather than by the foregoing description. All changes which come within the meaning and range of equivalency of the claims are to be embraced within their scope.

What is claimed is:

1. A compound of formula I

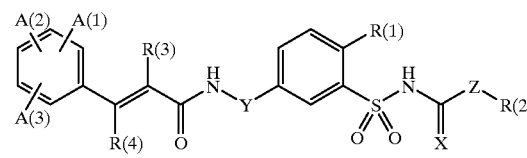

in which:

X is oxygen, sulfur, or cyanoimino;

Y is —(CR(5)$_2$)$_n$—;

Z is NH or oxygen;

the residues A(1), A(2), and A(3), which are independent of one another and can be identical or different, are hydrogen, halogen, ($C_1$–$C_4$)-alkyl, ($C_1$–$C_4$)-alkoxy, methylenedioxy, formyl, or trifluoromethyl;

R(1) is
a) (C$_1$–C$_4$)-alkyl;
b) —O—(C$_1$–C$_4$)-alkyl;
c) —O—(C$_1$–C$_4$)-alkyl-E(1)—(C$_1$–C$_4$)-alkyl-D(1), in which D(1) is hydrogen or —E(2)—(C$_1$–C$_4$)-alkyl-D(2), in which D(2) is hydrogen or —E(3)—(C$_1$–C$_4$)-alkyl, where E(1), E(2), and E(3), which are independent of one another and can be identical or different, are O, S, or NH;
d) —O—(C$_1$–C$_4$)-alkyl which is substituted by a residue of a saturated 4-membered to 7-membered heterocycle which contains one or two oxygens as ring heteroatoms;
e) —O—(C$_2$–C$_4$)-alkenyl;
f) —O—(C$_1$–C$_4$)-alkyl-phenyl in which the phenyl group is unsubstituted or substituted by one or two identical or different substituents selected from halogen, (C$_1$–C$_4$)-alkyl, (C$_1$–C$_4$)-alkoxy, and trifluoromethyl;
g) —O-phenyl which is unsubstituted or substituted by one or two identical or different substituents selected from halogen, (C$_1$–C$_4$)-alkyl, (C$_1$–C$_4$)-alkoxy, and trifluoromethyl;
h) halogen;
i) phenyl which is unsubstituted or substituted by one or two identical or different substituents selected from halogen, (C$_1$–C$_4$)-alkyl, (C$_1$–C$_4$)-alkoxy, —S(O)$_m$—(C$_1$–C$_4$)-alkyl, phenyl, amino, hydroxy, nitro, trifluoromethyl, cyano, hydroxycarbonyl, carbamoyl, (C$_1$–C$_4$)-alkoxycarbonyl, and formyl;
j) (C$_2$–C$_5$)-alkenyl which is unsubstituted or substituted by a substituent selected from phenyl, cyano, hydroxycarbonyl, and (C$_1$–C$_4$)-alkoxycarbonyl;
k) (C$_2$–C$_5$)-alkynyl which is unsubstituted or substituted by a substituent selected from phenyl and (C$_1$–C$_4$)-alkoxy;
l) monocyclic or bicyclic heteroaryl having one or two identical or different ring heteroatoms selected from oxygen, sulfur, and nitrogen;
m) —S(O)$_m$-phenyl which is unsubstituted or substituted by one or two identical or different substituents selected from halogen, (C$_1$–C$_4$)-alkyl, (C$_1$–C$_4$)-alkoxy, and trifluoromethyl; or
n) —S(O)$_m$—(C$_1$–C$_4$)-alkyl;
R(2) is hydrogen, (C$_1$–C$_6$)-alkyl, or (C$_3$–C$_7$)-cycloalkyl, but is not hydrogen if Z is oxygen;
the residues R(3) and R(4), which are independent of one another and can be identical or different, are phenyl which is unsubstituted or substituted by one or two identical or different substituents selected from halogen, (C$_1$–C$_4$)-alkyl, (C$_1$–C$_4$)-alkoxy, and trifluoromethyl, hydrogen, or (C$_1$–C$_4$)-alkyl;
the residues R(5), which are independent of one another and can be identical or different, are hydrogen or (C$_1$–C$_3$)-alkyl;
m is 0, 1, or 2;
n is 1, 2, 3, or 4;
in any stereoisomeric form or mixture thereof in any ratio, or a physiologically tolerable salt thereof,
where compounds of formula I are excluded in which, simultaneously, X is oxygen, Z is NH, R(1) is halogen, (C$_1$–C$_4$)-alkyl, or —O—(C$_1$–C$_4$)-alkyl, and R(2) is (C$_2$–C$_6$)-alkyl or (C$_5$–C$_7$)-cycloalkyl.

2. A compound of claim 1, in which R(3) is hydrogen, methyl, or unsubstituted phenyl, R(4) and R(5) are hydrogen, and n is 2 or 3.

3. A compound of claim 1, in which:
R(1) is
a) —O—(C$_1$–C$_4$)-alkyl;
b) —O—(C$_1$–C$_4$)-alkyl-O—(C$_1$–C$_4$)-alkyl-D(1), in which D(1) is hydrogen or —O—(C$_1$–C$_4$)-alkyl-D(2), in which D(2) is hydrogen or —O—(C$_1$–C$_4$)-alkyl;
c) —O—(C$_1$–C$_4$)-alkyl which is substituted by a residue of a saturated 4-membered to 7-membered heterocycle which contains one or two oxygens as ring heteroatoms;
d) —O—(C$_2$–C$_4$)-alkenyl;
e) —O—(C$_1$–C$_4$)-alkyl-phenyl in which the phenyl group is unsubstituted or substituted by one or two identical or different substituents selected from halogen, (C$_1$–C$_4$)-alkyl, (C$_1$–C$_4$)-alkoxy, and trifluoromethyl;
f) —O-phenyl which is unsubstituted or substituted by one or two identical or different substituents selected from halogen, (C$_1$–C$_4$)-alkyl, (C$_1$–C$_4$)-alkoxy, and trifluoromethyl;
g) phenyl which is unsubstituted or substituted by one or two identical or different substituents selected from halogen, (C$_1$–C$_4$)-alkyl, (C$_1$–C$_4$)-alkoxy, —S(O)$_m$—(C$_1$–C$_4$)-alkyl, phenyl, amino, hydroxy, nitro, trifluoromethyl, cyano, hydroxycarbonyl, carbamoyl, (C$_1$–C$_4$)-alkoxycarbonyl, and formyl; or
h) monocyclic or bicyclic heteroaryl having one or two identical or different ring heteroatoms selected from oxygen, sulfur, and nitrogen.

4. A compound of claim 1, in which Z is NH and R(2) is methyl.

5. A compound of claim 1, in which Z is NH and X is sulfur.

6. A compound of formula Ib of claim 1

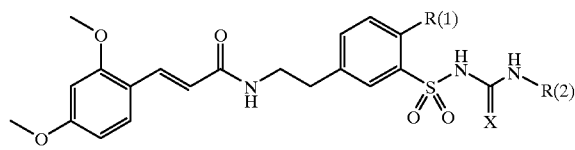

Ib in which:

X is oxygen or sulfur;

R(1) is methoxy, 2-methoxyethoxy-, tetrahydrofuran-2-ylmethoxy-, tetrahydropyran-2-ylmethoxy-, allyloxy, benzyloxy, or phenoxy; and R(2) is methyl, ethyl, isopropyl, or cyclohexyl;

in any stereoisomeric form or mixture thereof in any ratio, or a physiologically tolerable salt thereof.

7. A compound of claim 6, in which X is sulfur.

8. A process for the preparation of a compound of claim 1, comprising converting a benzenesulfonamide of formula III

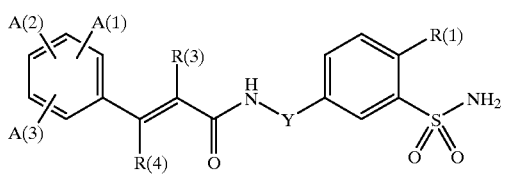

into a benzenesulfonyl iso(thio)cyanate of formula VIII

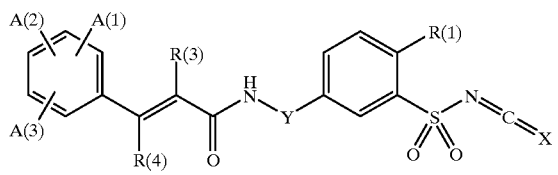

and reacting this with an amine of formula R(2)—NH$_2$ or an alcohol of formula R(2)—OH, and A(1), A(2), A(3), R(1), R(2), R(3), R(4), X, and Y being as defined in claim 1.

9. A process for the preparation of a compound of claim 1 in which Z is NH, comprising reacting a benzenesulfonamide of formula III as defined in claim 8 or a salt thereof with an iso(thio)cyanate of formula R(2)—N=C=X.

10. A process for the preparation of a compound of claim 1 in which Z is NH and X is oxygen, comprising reacting a benzenesulfonamide of formula III as defined in claim 8 or a salt thereof with a trichloroacetamide of formula Cl$_3$C—CO—NH—R(2).

11. A process for the preparation of a compound of claim 1 in which Z is NH and X is oxygen, comprising desulfurizing the corresponding compound of claim 1 in which Z is NH and X is sulfur on the thiourea group.

12. A pharmaceutical preparation, comprising at least one compound of claim 1 and/or a physiologically tolerable salt thereof and a pharmaceutically tolerable carrier.

13. A method for inhibiting ATP-sensitive potassium channels or stimulating the vagal nervous system, comprising administering to a patient in need thereof an effective amount of at least one compound of formula I

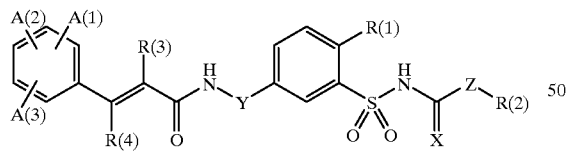

in which:
X is oxygen, sulfur, or cyanoimino;
Y is —(CR(5)$_2$)$_n$—;
Z is NH or oxygen;
the residues A(1), A(2), and A(3), which are independent of one another and can be identical or different, are hydrogen, halogen, (C$_1$–C$_4$)-alkyl, (C$_1$–C$_4$)-alkoxy, methylenedioxy, formyl, or trifluoromethyl;
R(1) is
a) (C$_1$–C$_4$)-alkyl;
b) —O—(C$_1$–C$_4$)-alkyl;
c) —O—(C$_1$–C$_4$)-alkyl-E(1)—(C$_1$–C$_4$)-alkyl-D(1), in which D(1) is hydrogen or —E(2)—(C$_1$–C$_4$)-alkyl-D(2), in which D(2) is hydrogen or —E(3)—(C$_1$–C$_4$)-alkyl, where E(1), E(2), and E(3), which are independent of one another and can be identical or different, are O, S, or NH;
d) —O—(C$_1$–C$_4$)-alkyl which is substituted by a residue of a saturated 4-membered to 7-membered heterocycle which contains one or two oxygens as ring heteroatoms;
e) —O—(C$_2$–C$_4$)-alkenyl;
f) —O—(C$_1$–C$_4$)-alkyl-phenyl in which the phenyl group is unsubstituted or substituted by one or two identical or different substituents selected from halogen, (C$_1$–C$_4$)-alkyl, (C$_1$–C$_4$)-alkoxy, and trifluoromethyl;
g) —O-phenyl which is unsubstituted or substituted by one or two identical or different substituents selected from halogen, (C$_1$–C$_4$)-alkyl, (C$_1$–C$_4$)-alkoxy, and trifluoromethyl;
h) halogen;
i) phenyl which is unsubstituted or substituted by one or two identical or different substituents selected from halogen, (C$_1$–C$_4$)-alkyl, (C$_1$–C$_4$)-alkoxy, —S(O)$_m$—(C$_1$–C$_4$)-alkyl, phenyl, amino, hydroxy, nitro, trifluoromethyl, cyano, hydroxycarbonyl, carbamoyl, (C$_1$–C$_4$)-alkoxycarbonyl, and formyl;
j) (C$_2$–C$_5$)-alkenyl which is unsubstituted or substituted by a substituent selected from phenyl, cyano, hydroxycarbonyl, and (C$_1$–C$_4$)-alkoxycarbonyl;
k) (C$_2$–C$_5$)-alkynyl which is unsubstituted or substituted by a substituent selected from phenyl and (C$_1$–C$_4$)-alkoxy;
l) monocyclic or bicyclic heteroaryl having one or two identical or different ring heteroatoms selected from oxygen, sulfur, and nitrogen;
m) —S(O)$_m$-phenyl which is unsubstituted or substituted by one or two identical or different substituents selected from halogen, (C$_1$–C$_4$)-alkyl, (C$_1$–C$_4$)-alkoxy, and trifluoromethyl; or
n) —S(O)$_m$—(C$_1$–C$_4$)-alkyl;
R(2) is hydrogen, (C$_1$–C$_6$)-alkyl, or (C$_3$–C$_7$)-cycloalkyl, but is not hydrogen if Z is oxygen;
the residues R(3) and R(4), which are independent of one another and can be identical or different, are phenyl which is unsubstituted or substituted by one or two identical or different substituents selected from halogen, (C$_1$–C$_4$)-alkyl, (C$_1$–C$_4$)-alkoxy, and trifluoromethyl, hydrogen, or (C$_1$–C$_4$)-alkyl;
the residues R(5), which are all independent of one another and can be identical or different, are hydrogen or (C$_1$–C$_3$)-alkyl;
m is 0, 1, or 2;
n is 1, 2, 3, or 4;
in any stereoisomeric form or mixture thereof in any ratio, and/or a physiologically tolerable salt thereof.

14. A method for reducing, eliminating, or avoiding a dysfunction of the autonomic nervous system of the heart, comprising administering to a patient in need thereof an effective amount of at least one compound of claim 13.

15. A method for treating or preventing cardiovascular disorders, ischemic conditions of the heart, coronary heart disease, a weakened myocardial contractile force, cardiac insufficiency, cardiomyopathies, or cardiac arrhythmias, comprising administering to a patient in need thereof an effective amount of at least one compound of claim 13.

16. A method for preventing sudden cardiac death, comprising administering to a patient in need thereof an effective amount of at least one compound of claim 13.

17. A method for improving the heart function, comprising administering to a patient in need thereof an effective amount of at least one compound of claim 13.

18. A compound of formula If

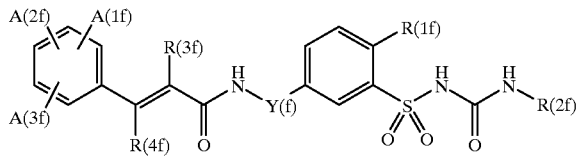

If in which:

Y(f) is —(CR(5f)$_2$)$_{n(f)}$—;

the residues A(1f), A(2f), and A(3f), which are independent of one another and can be identical or different, are hydrogen, halogen, (C$_1$–C$_4$)-alkyl, (C$_1$–C$_4$)-alkoxy, methylenedioxy, formyl, or trifluoromethyl;

R(1f) is —O—(C$_1$–C$_4$)-alkyl;

R(2f) is (C$_2$–C$_6$)-alkyl or (C$_5$–C$_7$)-cycloalkyl;

the residues R(3f) and R(4f), which are independent of one another and can be identical or different, are hydrogen or (C$_1$–C$_4$)-alkyl;

the residues R(5f), which are independent of one another and can be identical or different, are hydrogen or (C$_1$–C$_3$)-alkyl;

n(f) is 1, 2, 3, or 4;

in any stereoisomeric form or mixture thereof in any ratio, or a physiologically tolerable salt thereof.

19. A compound of claim 1, in which X is sulfur or cyanoimino.

20. A method of claim 13, in which X is sulfur or cyanoimino.

* * * * *